(12) United States Patent
Morita et al.

(10) Patent No.: US 9,267,043 B2
(45) Date of Patent: Feb. 23, 2016

(54) POLYMERIZABLE COMPOUND, INK CARTRIDGE CONTAINING INK INCLUDING THE POLYMERIZABLE COMPOUND, INKJET RECORDING APPARATUS USING THE INK CARTRIDGE, AND PRINT FORMED BY INK INCLUDING THE POLYMERIZABLE COMPOUND

(71) Applicants: Mitsunobu Morita, Shizuoka (JP); Soh Noguchi, Kanagawa (JP); Okitoshi Kimura, Kanagawa (JP)

(72) Inventors: Mitsunobu Morita, Shizuoka (JP); Soh Noguchi, Kanagawa (JP); Okitoshi Kimura, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 39 days.

(21) Appl. No.: 14/028,773

(22) Filed: Sep. 17, 2013

(65) Prior Publication Data
US 2014/0120326 A1 May 1, 2014

(30) Foreign Application Priority Data

Oct. 26, 2012 (JP) ................................. 2012-236206
Aug. 2, 2013 (JP) ................................. 2013-161522

(51) Int. Cl.
| | | |
|---|---|---|
| *C09D 11/30* | (2014.01) | |
| *C07C 233/09* | (2006.01) | |
| *C07C 233/20* | (2006.01) | |
| *C07D 211/40* | (2006.01) | |
| *C07D 211/46* | (2006.01) | |
| *C07D 295/185* | (2006.01) | |
| *C09D 11/101* | (2014.01) | |
| *C09D 11/322* | (2014.01) | |

(52) U.S. Cl.
CPC .............. *C09D 11/30* (2013.01); *C07C 233/09* (2013.01); *C07C 233/20* (2013.01); *C07D 211/40* (2013.01); *C07D 211/46* (2013.01); *C07D 295/185* (2013.01); *C09D 11/101* (2013.01); *C09D 11/322* (2013.01); *Y10T 428/24802* (2015.01)

(58) Field of Classification Search
CPC .. C07C 233/09; C07C 233/20; C07D 211/40; C07D 295/185; C07D 211/46; C09D 11/101; C09D 11/30
USPC ........................................................ 523/160
See application file for complete search history.

(56) References Cited

U.S. PATENT DOCUMENTS

| | | | |
|---|---|---|---|
| 2,773,063 A | 12/1956 | Specht et al. | |
| 4,288,232 A * | 9/1981 | Schmolka et al. | 44/281 |
| 4,562,142 A * | 12/1985 | Kakumaru et al. | 430/288.1 |
| 5,288,917 A * | 2/1994 | Berner et al. | 568/331 |
| 5,523,152 A | 6/1996 | Thurber et al. | |
| 2008/0165233 A1* | 7/2008 | Lin et al. | 347/86 |
| 2011/0060100 A1 | 3/2011 | Kimura et al. | |
| 2011/0092610 A1 | 4/2011 | Habashi et al. | |
| 2011/0211013 A1 | 9/2011 | Matsumoto et al. | |
| 2012/0086762 A1 | 4/2012 | Noguchi et al. | |
| 2012/0147095 A1 | 6/2012 | Miura et al. | |
| 2012/0147103 A1 | 6/2012 | Hasegawa et al. | |
| 2012/0176456 A1 | 7/2012 | Maekawa et al. | |
| 2012/0242768 A1 | 9/2012 | Seno et al. | |
| 2012/0249700 A1 | 10/2012 | Amao et al. | |
| 2012/0283378 A1 | 11/2012 | Shoshi et al. | |
| 2012/0295048 A1 | 11/2012 | Al-Malaika et al. | |
| 2013/0005849 A1 | 1/2013 | Noguchi et al. | |
| 2013/0065024 A1 | 3/2013 | Aruga et al. | |
| 2013/0144057 A1 | 6/2013 | Morita | |
| 2013/0222501 A1 | 8/2013 | Kamada | |

FOREIGN PATENT DOCUMENTS

| | | |
|---|---|---|
| DE | 19517072 | 11/1996 |
| EP | 2365041 A1 | 9/2011 |
| EP | 2505622 A1 | 10/2012 |
| EP | 2602244 A1 | 6/2013 |
| JP | 2003-266915 | 9/2003 |
| JP | 2004-067991 | 3/2004 |
| JP | 2006-224662 | 8/2006 |
| JP | 2006-257155 | 9/2006 |
| JP | 2007-138118 | 6/2007 |
| JP | 2007-177174 | 7/2007 |
| JP | 2007-231231 | 9/2007 |
| JP | 2007-231233 | 9/2007 |
| JP | 2009-067926 | 4/2009 |

(Continued)

OTHER PUBLICATIONS

European Search Report dated Jan. 22, 2014 in corresponding European patent application No. 13 18 84 81.9.
Grace N.Y. Chan et al., "The Synthesis of Novel Hybrid Monomers", Australian Journal of Chemistry, vol. 51, 1998, p. 31-35.
Monge S et al., "Synthesis of precursors of iodine-labeled multifunctional ligans containing 2-nitroimidazole for the detection of hypoxic tissues and/or tumors", Tetrahedron, Elsevier Science Publishers, Amsterdam, NL, vol. 57, No. 50, Dec. 10, 2001, p. 9979-9987.

(Continued)

*Primary Examiner* — Alexander Kollias
(74) *Attorney, Agent, or Firm* — Cooper & Dunham LLP

(57) ABSTRACT

A polymerizable compound is provided. The polymerizable compound has two or more polymerizable functional groups in a molecule thereof, wherein one of the two or more polymerizable functional groups of the polymerizable compound is an acrylamide group having the below-mentioned formula (1). The polymerizable compound can be preferably used for inkjet ink.

(1)

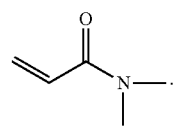

11 Claims, 2 Drawing Sheets

(56) References Cited

FOREIGN PATENT DOCUMENTS

| | | |
|---|---|---|
| JP | 2009-144057 | 7/2009 |
| JP | 2009-179681 | 8/2009 |
| JP | 2009-249561 | 10/2009 |
| JP | 2010-013506 | 1/2010 |
| JP | 2010-058405 | 3/2010 |
| JP | 2010-069623 | 4/2010 |
| JP | 2010-181677 | 8/2010 |
| JP | 2012-025862 | 2/2012 |
| JP | 2012-140550 | 7/2012 |
| JP | 2012-140551 | 7/2012 |
| JP | 2012-140583 | 7/2012 |
| JP | 2012-144712 | 8/2012 |
| WO | WO03/089486 A1 | 10/2003 |
| WO | WO2011/092476 | 8/2011 |

OTHER PUBLICATIONS

Wang C et al., "Chemoselective Lactam Formation in the Addition of Benzenesulfonyl Bromide to N-Allyl Acrylamides and N-Allyl 3,3-Dimethylacrylamides", The Journal of Organic Chemistry, American Chemical Society [NOT]Etc., US, vol. 64, No. 7, Dec. 3, 1999, p. 2346-2352.

* cited by examiner

POLYMERIZABLE COMPOUND, INK CARTRIDGE CONTAINING INK INCLUDING THE POLYMERIZABLE COMPOUND, INKJET RECORDING APPARATUS USING THE INK CARTRIDGE, AND PRINT FORMED BY INK INCLUDING THE POLYMERIZABLE COMPOUND

CROSS-REFERENCE TO RELATED APPLICATIONS

This patent application is based on and claims priority pursuant to 35 U.S.C. §119 to Japanese Patent Applications Nos. 2012-236206 and 2013-161522 filed on Oct. 26, 2012 and Aug. 2, 2013 in the Japan Patent Office, the entire disclosure of which is hereby incorporated by reference herein.

TECHNICAL FIELD

This disclosure relates to a polymerizable compound. In addition, this disclosure relates to an ink cartridge containing an ink including the polymerizable compound, and to an inkjet recording apparatus using the ink cartridge. Further, this disclosure relates to a print formed by an ink including the polymerizable compound.

BACKGROUND

Electrophotographic recording methods, sublimation transfer recording methods, thermal transfer recording methods, and inkjet recording methods are exemplified as methods for forming images on recording media such as paper. Among these recording methods, inkjet recording methods have advantages over other recording methods such that efficiency of consumption of the image recording material (i.e., ink) is high (i.e., the method is superior in resource saving); and the cost of the image recording material used for forming an image with a unit area is low. However, inkjet recording methods using an aqueous ink have various problems to be solved. Inkjet recording methods using an ink including an organic solvent have been proposed in attempting to solve the problems, but such organic solvent inks have other problems to be solved.

In recent years, inkjet recording methods using an active energy ray curable ink attract attention. For example, ultraviolet curable inks, which are representative examples of the active energy ray curable ink, have been described in various documents, and typically include a monomer and a polymerization initiator as essential components while optionally including other components such as pigments, oligomers, polymers, and sensitizers as described in OPTICAL APPLICATION TECHNOLOGY AND MATERIAL DICTIONARY published in Japan in 2006 by Industrial Technology Service Center and OPTIMIZATION OF UV CURING RESIN published in Japan in 2008 by TECHNICAL INFORMATION INSTITUTE CO., LTD. Specific examples of the UV curable ink described in OPTICAL APPLICATION TECHNOLOGY AND MATERIAL DICTIONARY include inks including a radically polymerizable compounds such as acrylate compounds (e.g., ethylene oxide adduct of trimethylolpropane triacrylate, trimethylolpropane triacrylate, 1,9-nonanediol diacrylate, isobonyl acrylate, and compounds (oligomers) having the below-mentioned formulae), N-vinyl formamide, and triallylisocyanurate, and inks including a cationically polymerizable compound such as bis(3-ethyl-3-oxetanylmethyl)ether, and CELLOXIDE 2021 (difunctional alicyclic epoxy compound) from DAICEL CORP.

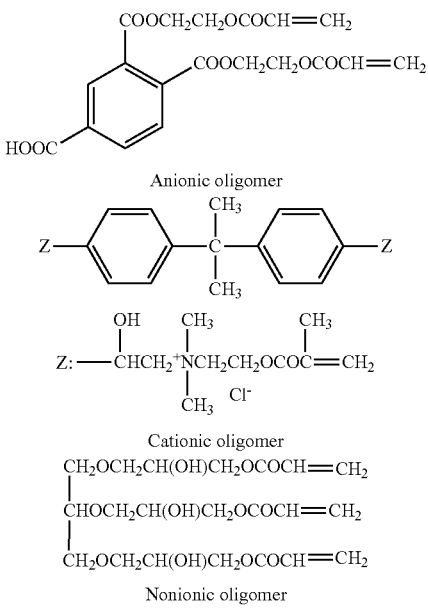

The monomer component in such active energy ray curable inks typically includes plural monomers to optimize the curing speed (i.e., sensitivity), the ink viscosity, and the properties of a film formed by curing the ink. Specifically, a combination of a monomer, which has a low molecular weight and a low viscosity and which has good reactivity, and a monomer which is multifunctional and which has a high molecular weight is typically used. Since the content of the monomer component in such an active energy ray curable ink is about 80% by weight (i.e., since monomers are main components of such an ink), not only development of new monomers but also development of compounding techniques has been actively performed.

For example, JP-2007-231231-A discloses an ink including an ester or amide compound of (meth)acrylic acid which is tri- or more-functional compound having an alkylene oxide group therein. JP-2007-231233-A discloses an ink including a combination of an ester or amide compound of (meth) acrylic acid which is a tri- or more-functional compound having an alkylene oxide group therein, and an ester or amide compound of (meth)acrylic acid which is a mono-functional compound having an alkyl group having 6 to 12 carbon atoms. JP-2007-67926-A discloses an ink including an aliphatic (meth)acrylate compound having a secondary hydroxyl group, and a compound having a nitrogen atom and a polymerizable unsaturated bond therein. JP-2007-144057-A discloses an ink including a polymerizable compound having an amino group and a polymerizable unsaturated bond therein.

In addition, there are proposals for inks using a monomer compound having a urethane structure. For example, JP-2006-257155-A and JP2009-249561-A have disclosed inks including a urethane acrylate oligomer. JP-2010-181677-A discloses an ink including a low molecular weight (meth)acrylate monomer having a urethane structure. In attempting to enhance the curability of ink, and the flexibility of the cured film of ink, JP-2007-138118-A discloses an ink including a monomer having an aliphatic ring structure, and JP-2007-177174-A discloses an ink including a monomer having a heterocyclic structure such as dioxolan or dioxane. In attempting to reduce the viscosity of ink while enhancing the curability of ink, and the solvent resistance and adhesiveness of the cured film of ink, JP-2009-179681-A discloses an ink including two or more of monomers which have an aliphatic ring structure, a heterocyclic structure or an aromatic ring structure.

In addition, there are proposals for inks including a monomer having two different polymerizable functional groups therein. For example, inks and a diluent, which use a compound having both a (meth)acrylic acid ester group and a vinyl ether group have been disclosed in JP-3461501-B1, JP-3544658-B1 (i.e., WO2003/089486), JP-2012-140551-A and JP-2012-140583-A.

When the above-mentioned inks including a polymerizable compound (monomer) are used, odor is a major problem to be solved. In general, active energy ray curable inks include a large mount of diluent, which is typically a low molecular weight reactive monomer and which serves as a solvent of the inks, to properly control the viscosity of the inks. However, such low molecular weight monomer compounds typically have an unpleasant odor.

For these reasons, the inventors recognized that there is a need for an ink which has a good combination of reactivity (photo-polymerizability) and curability (hardenability) and which hardly smells.

SUMMARY

The object of this disclosure is to provide a polymerizable compound which has good photo-polymerizability and curability and hardly smells and which can be used for ink.

As an aspect of this disclosure, a polymerizable compound is provided which has two or more polymerizable functional groups in a molecule thereof, wherein one of the polymerizable functional groups is an acrylamide group having the following formula (1):

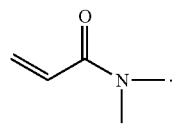

(1)

As another aspect of this disclosure, an ink cartridge is provided which includes a container and an ink, which is contained in the container and which includes the above-mentioned polymerizable compound.

As another aspect of this disclosure, an inkjet recording apparatus is provided which includes the above-mentioned ink cartridge, and an inkjet recording device to eject droplets of the ink contained in the ink cartridge to form an ink image on a recording medium.

As another aspect of this disclosure, a print is provided which includes a support and an image formed on the support by the above-mentioned ink.

The aforementioned and other aspects, features and advantages will become apparent upon consideration of the following description of the preferred embodiments taken in conjunction with the accompanying drawings.

DETAILED DESCRIPTION

Figure 1:
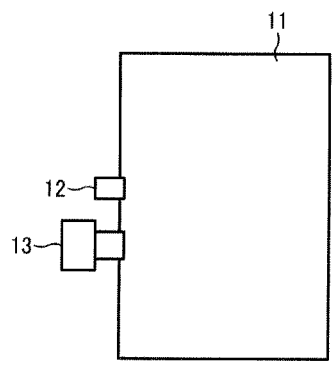
FIG. 1 is a schematic view illustrating an ink bag for use in an ink cartridge according to an embodiment.

Inks including such low molecular monomer compounds as mentioned above have an odor problem. Since human being smells odor of a compound by detecting the molecules of the compound, which are scattered in the air, with the noses thereof, it is preferable that such monomer compounds as having an unpleasant odor are hardly scattered in the air. Therefore, the present inventors consider that by increasing the molecular weight of such a monomer or by incorporating a polar functional group into a monomer to strengthen the intermolecular interaction thereof, so that scattering of the compound in the air is reduced, odor of the ink including the monomer can be improved.

However, when an ink is prepared only by using a high molecular weight monomer compound, the ink has too high a viscosity to be used as an inkjet ink. Therefore, the present inventors consider that it is preferable to incorporate a polar functional group into a monomer to strengthen the intermolecular interaction thereof.

As a result of the present inventors' investigation, it is found that by incorporating polymerizable functional groups, which include an acrylamide group and another polymerizable functional group, into a polymerizable compound, the polymerizable compound hardly smells, and an ink including the polymerizable compound has good reactivity and curability when exposed to an active energy ray.

The polymerizable compound of this disclosure, which can be used for ink and polymerizable compositions, has two or more polymerizable functional groups in a molecule thereof, wherein one of the polymerizable functional groups is an acrylamide group having the following formula (1):

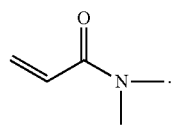

(1)

The ink for use in the ink cartridge and the inkjet recording apparatus of this disclosure includes at least the polymerizable compound of this disclosure, and optionally includes a polymerization initiator and other components. In addition, the polymerizable compound can be used for polymerizable compositions for use in curable coating liquids and adhesives as well as the ink.

Next, the polymerizable compound of this disclosure will be described by reference to an ink using the polymerizable compound.

The polymerizable compound of this disclosure can be cured (dried) when irradiated with an active energy ray. Ink including the polymerizable compound can be used for various printing ink such as offset printing and screen printing inks, and is preferably used as an inkjet printing ink (hereinafter sometimes referred to as an ink). Namely, the ink is preferably used for inkjet recording methods.

In the ink of this disclosure, another of the polymerizable functional groups of the polymerizable compound is a group having a (meth)acrylic acid ester structure having the following formula (2):

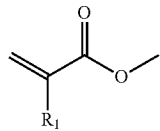
(2)

wherein $R_1$ represents a hydrogen atom or a methyl group.

It is preferable for the ink that the polymerizable compound has the following formula (3) or (4):

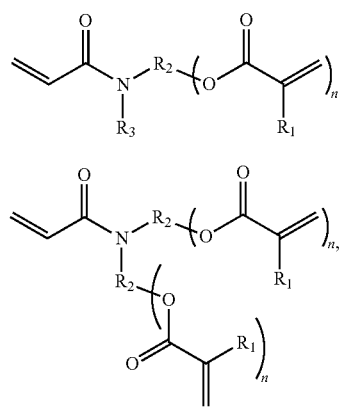
(3)
(4)

wherein $R_1$ represents a hydrogen atom or a methyl group; $R_2$ represents a divalent or trivalent group having 1 to 15 carbon atoms, which optionally has a ring structure and a hetero atom; $R_3$ represents a hydrogen atom, or an alkyl group having 1 to 15 carbon atoms, which optionally has a ring structure and a hetero atom; and n is 1 or 2.

It is preferable for the ink that the polymerizable compound has the following formula (5) or (6):

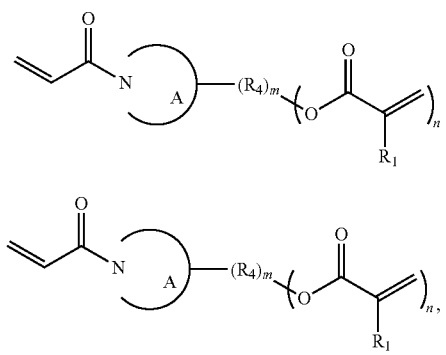
(5)
(6)

wherein $R_1$ represents a hydrogen atom or a methyl group; $R_4$ represents a divalent or trivalent group having 1 to 15 carbon atoms, which optionally has a ring structure and a hetero atom; A represents a group having a ring structure having at least one nitrogen atom; n is 1 or 2; and m is 0 or 1.

The group A preferably has a piperazine ring structure.

It is preferable for the ink that the polymerizable compound has the following formula (7) or (8):

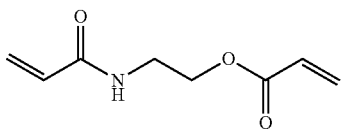
(7)

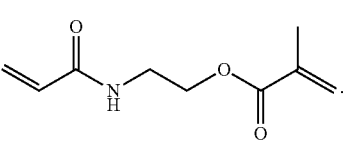
(8)

It is preferable for the ink that the polymerizable compound has the following formula (9):

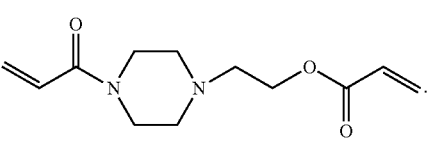
(9)

The ink cartridge of this disclosure includes a container, and the above-mentioned ink contained in the container.

The inkjet recording apparatus of this disclosure includes the ink cartridge mentioned above, and an inkjet recording device to eject the ink in the ink cartridge as droplets to form an image on a recording medium.

The print of this disclosure includes a support, and an ink image formed on the support by the ink mentioned above.

The polymerizable compound of this disclosure is a compound having two or more polymerizable functional groups in a molecule thereof, wherein one of the polymerizable functional groups is an acrylamide group having the above-mentioned formula (1).

The polymerizable compound preferably has another polymerizable functional group having a (meth)acrylic acid ester structure having the above-mentioned formula (2).

The polymerizable compound preferably has the above-mentioned formula (3), (4), (5), (6), (7), (8) or (9).

Next, the polymerizable compound (i.e., monomer) for use in the ink of this disclosure will be described.

The polymerizable compound includes two or more polymerizable functional groups in a molecule thereof, and one of the groups is an acrylamide group having the above-mentioned formula (1). The polymerizable compound preferably has an acrylamide group, and a (meth)acrylic acid ester group in a molecule thereof. It is more preferable that the polymerizable compound has one of the formulae of from (3) to (6). It is even more preferable that the polymerizable compound has one of the formulae of from (7) to (9).

In formula (2), $R_1$ represents a hydrogen atom or a methyl group.

In formulae (3) to (6), $R_1$ represents a hydrogen atom or a methyl group, $R_2$ represents a divalent or trivalent group having 1 to 15 carbon atoms, which optionally includes a ring structure and a hetero atom, $R_3$ represents a hydrogen atom, or an alkyl group having 1 to 15 carbon atoms, which optionally includes a ring structure and a hetero atom, $R_4$ represents a divalent or trivalent group having 1 to 15 carbon atoms, which optionally includes a ring structure and a hetero atom, A represents a group having a ring structure having at least one nitrogen atom, n is 1 or 2, and m is 0 or 1.

It is considered that since the polymerizable compound in the ink includes two or more polymerizable functional groups in a molecule thereof, and one of the groups is an acrylamide group having the above-mentioned formula (1), the ink has an advantage such that the ink hardly smells. The reason therefor is not yet determined, but is considered to be that since an acrylamide group has a relatively strong intermolecular interaction compared to acrylic ester groups, evaporation of the compound can be reduced, thereby reducing odor even when the compound has a low molecular weight. In addition, when a polymerizable functional group other than the acrylamide group is present in the molecule of the compound in combination of the acrylamide group, the curability of the compound can be enhanced. The polymerizable functional group other than the acrylamide group is preferably a group having a (meth)acrylic acid ester structure. In this case, the two functional groups have structures preferable for radical polymerization, and therefore the compound has better curability.

In general, methacrylic acid esters are inferior to acrylic acid esters in polymerizability and curability. However, when a compound having a methacrylic acid ester group is used for the ink of this disclosure, the ink has good curability. The reason therefor is considered to be that the ink includes a polymerizable compound having both an acrylamide group and a (meth)acrylic acid ester group in a molecule thereof. This is one of the features of the ink of this disclosure.

Polymerizable compounds having plural acrylamide groups in a molecule thereof have strong intermolecular interaction, and therefore such compounds tend to solidify at room temperature. Therefore, it is preferable to incorporate an acrylamide group and another polymerizable functional group in a molecule of a polymerizable compound, because the compound achieves a liquid state at room temperature while having reduced odor and a good combination of reactivity and curability. Among such polymerizable compounds, compounds having one of formulae (7) and (8) are preferable because the acrylamide group has one NH structure, and the compound has a (meth)acrylic acid ester structure. Thus, the ink of this disclosure, which uses such a polymerizable compound, has good curability while having reduced odor, and therefore the ink has good practicality. In addition, the compound having formula (9) has good curability because of having a piperazine ring having two nitrogen atoms. In addition, the compound has a high polarity because of having two nitrogen atoms, and therefore the compound hardly smells. Further, the nitrogen atom of the quaternary amine structure of the piperazine ring of the compound has a side chain having good freedom, the molecule of the compounds has good flexibility, and therefore the compound can achieve a liquid state at room temperature.

Preferable examples of the polymerizable compound for use in the ink of this disclosure will be described.

Specific examples of compounds having formula (3), in which $R_3$ is a hydrogen atom and n is 1, include the following compounds A-1 to A-14. In this regard, the compounds A-13 and A-14 are examples of compounds in which the group $R_2$ has a ring structure.

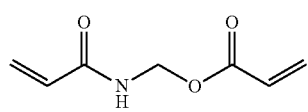

A-1

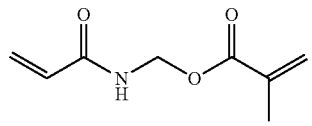

A-2

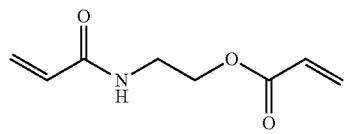

A-3

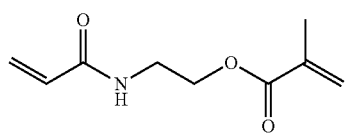

A-4

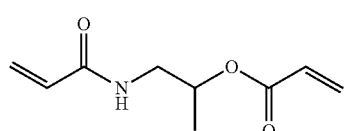

A-5

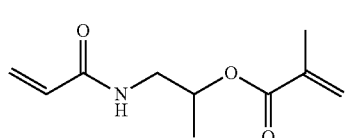

A-6

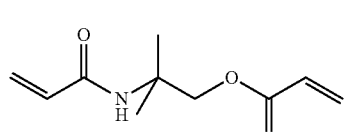

A-7

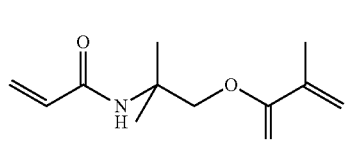

A-8

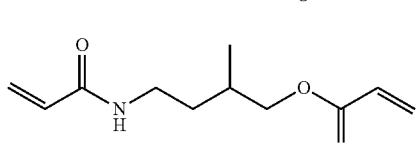

A-9

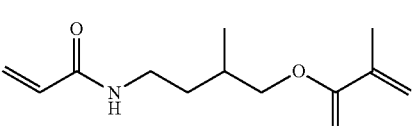

A-10

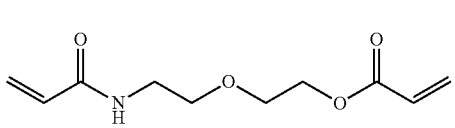

A-11

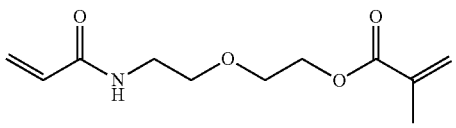

A-12

A-13
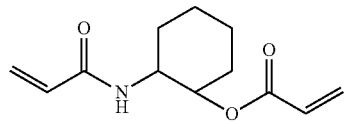

A-14
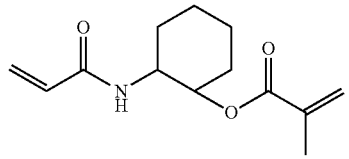

Specific examples of compounds having formula (3), in which $R_3$ is a hydrogen atom, $R_2$ includes an oxygen atom as a hetero atom, and n is 1, include the following compounds A-15 and A-16.

A-15
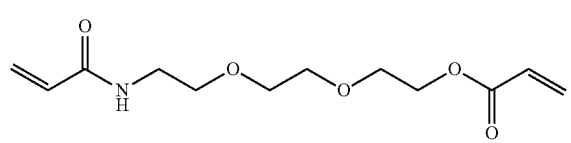

A-16
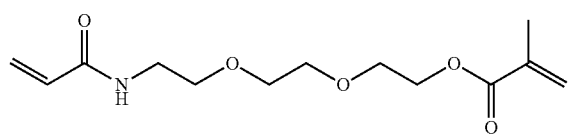

Specific examples of compounds having formula (3), in which $R_1$ is a hydrogen atom and n is 2, include the following compounds B-1 to B-6. In this regard, the compounds B-1 to B-4 are examples of compounds in which the group $R_2$ does not include a hetero atom, and the compounds B-5 and B-6 are examples of compounds in which the group $R_2$ includes a nitrogen atom as a hetero atom.

B-1
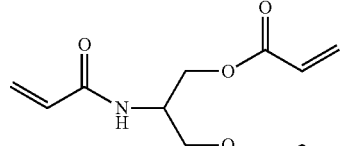

B-2
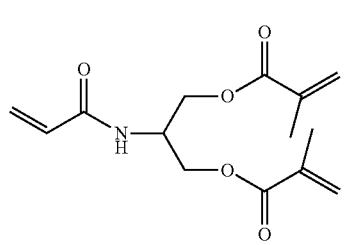

B-3
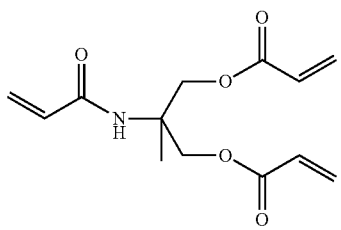

B-4
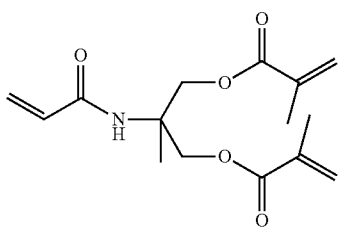

B-5
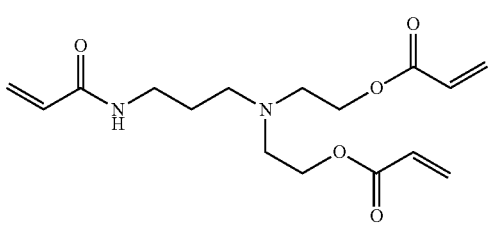

B-6
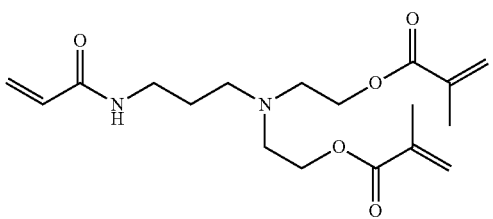

Specific examples of compounds having formula (3), in which $R_3$ is an alkyl group and n is 2, include the following compounds C-1 to C-16.

C-1
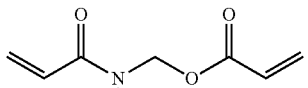

C-2
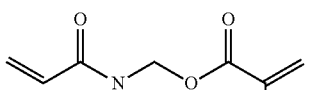

C-3
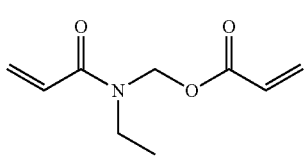

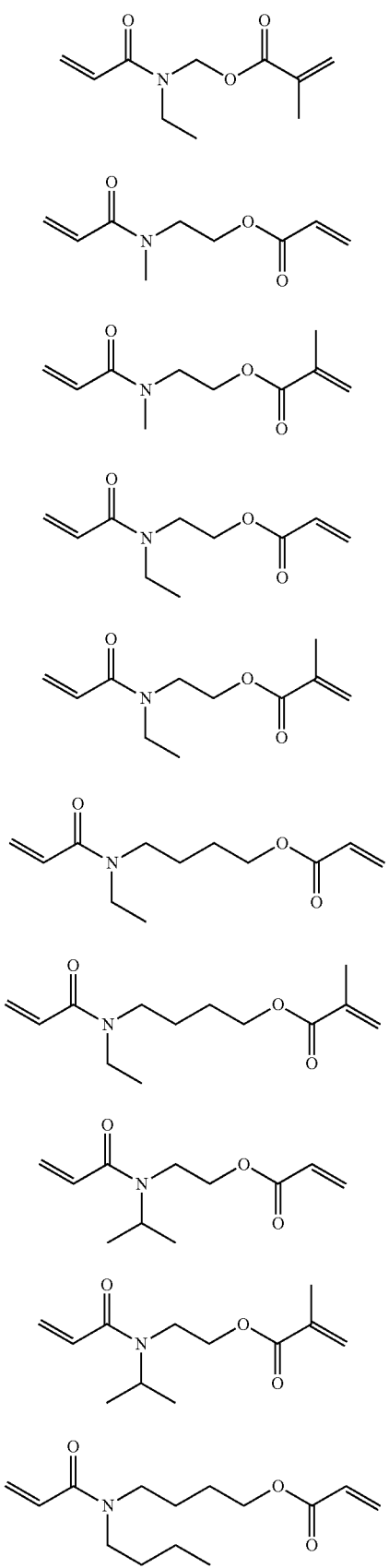

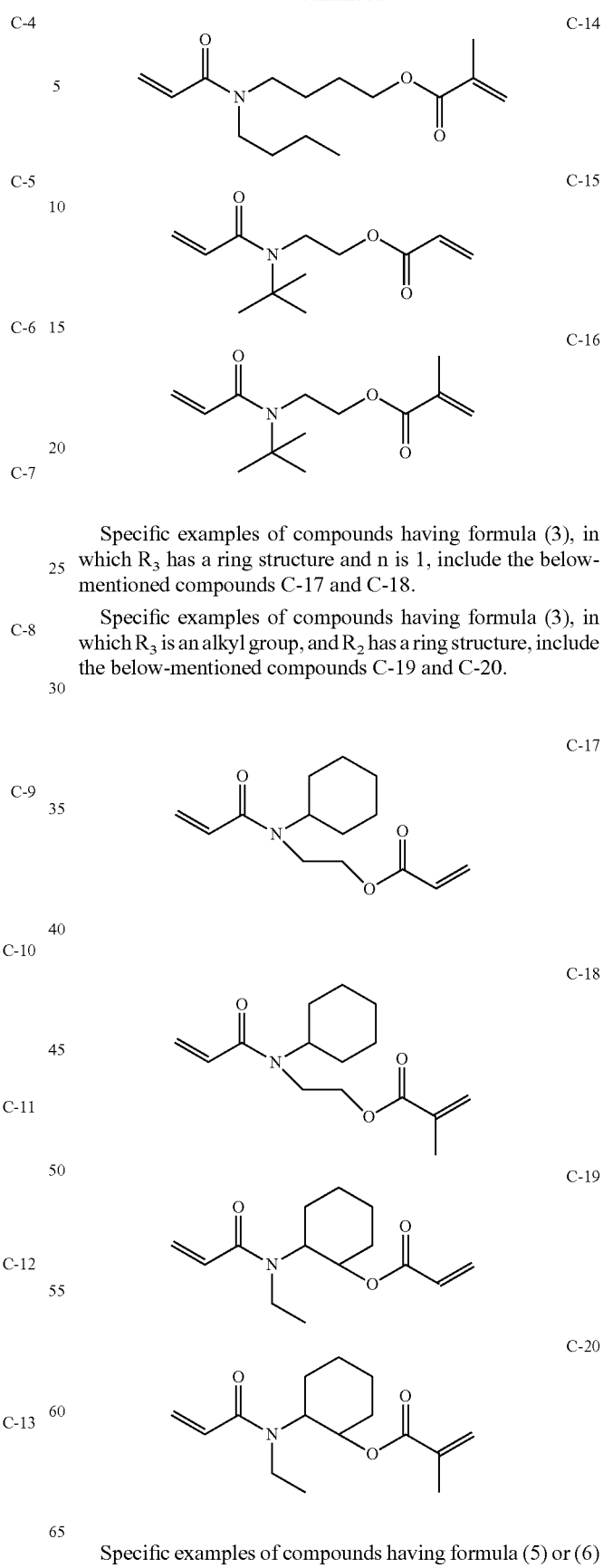

Specific examples of compounds having formula (3), in which $R_3$ has a ring structure and n is 1, include the below-mentioned compounds C-17 and C-18.

Specific examples of compounds having formula (3), in which $R_3$ is an alkyl group, and $R_2$ has a ring structure, include the below-mentioned compounds C-19 and C-20.

Specific examples of compounds having formula (5) or (6) include the following compounds D-1 to D14.

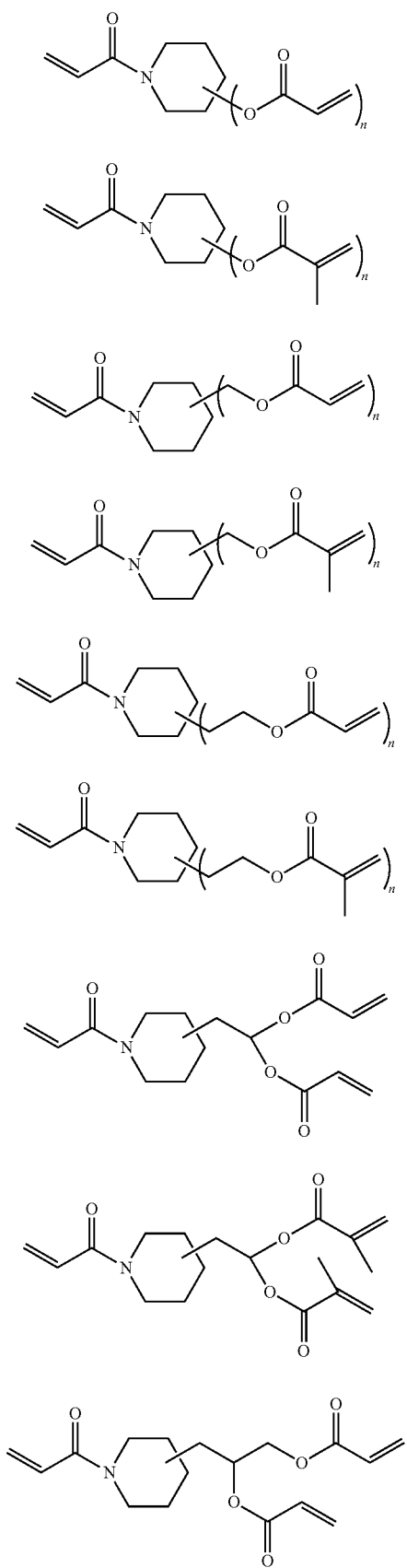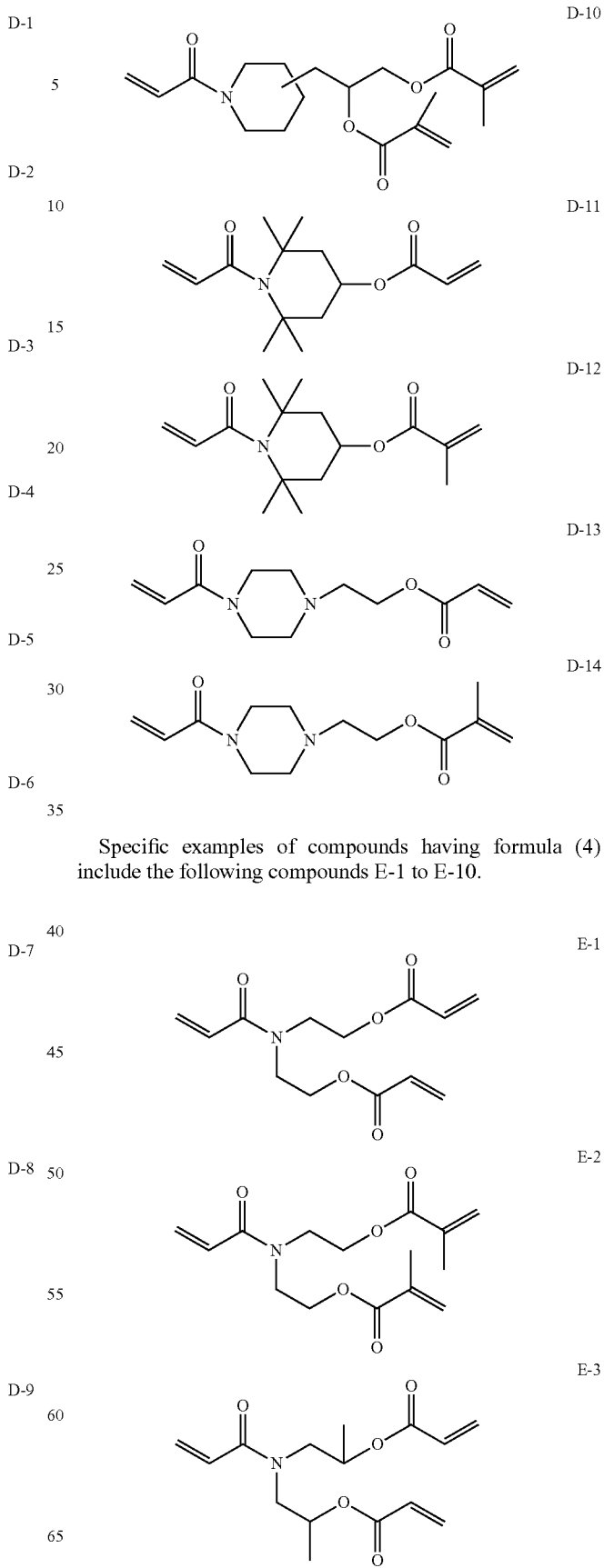
Specific examples of compounds having formula (4) include the following compounds E-1 to E-10.

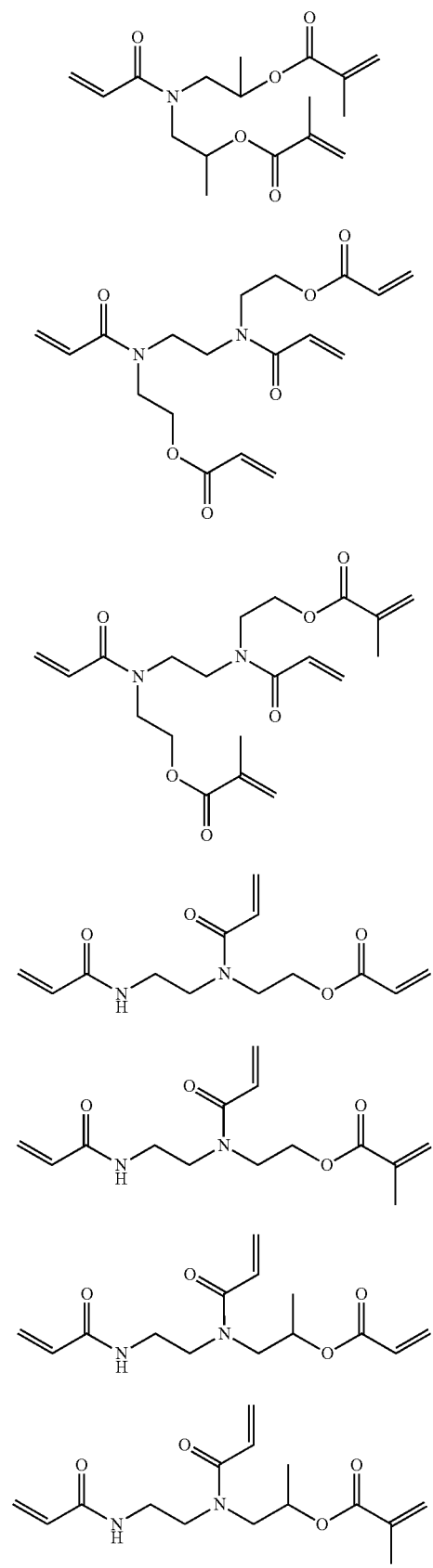
Specific examples of polymerizable functional groups other than the above-mentioned groups having a (meth) acrylic acid ester structure include an allyl group, a vinyl ether group, and an epoxy group.
Specific examples of polymerizable compounds having an allyl group or a vinyl ether group include the following compounds F-1 to F-10.
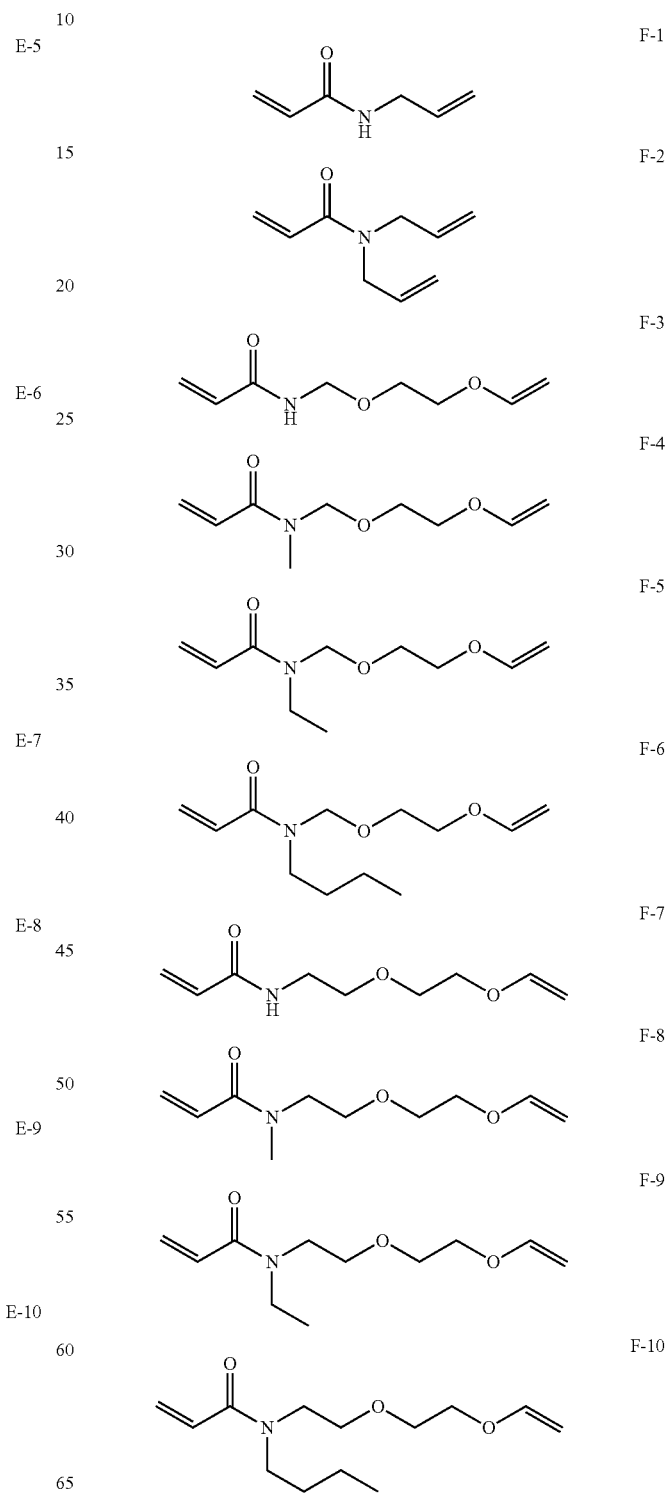

In this regard, the polymerizable functional group is preferably bonded with the acrylamide group with an ether bond therebetween.

Next, the polymerization initiator for use in the ink of this disclosure will be described.

The ink for used in the ink cartridge and the inkjet recording apparatus of this disclosure optionally includes a polymerization initiator. The ink can be used for various inks such as inkjet inks, and curable compositions.

Suitable materials for use as the polymerization initiator include radical polymerization initiators, cationic polymerization initiators, and anionic polymerization initiators. Among these initiators, radical polymerization initiators, and anionic polymerization initiators are preferable, and radical polymerization initiators are more preferable.

Among the above-mentioned polymerization initiators, a proper initiator is selected depending on the polymerizable compound used, and the purpose of the ink.

The polymerization initiator included in the ink is a compound which generates a polymerization starting material upon absorption of external energy such as heat energy and active energy rays. Namely, heat polymerization initiators and photo-polymerization initiators can be used for heat energy and active energy rays, respectively. Specific examples of the active energy rays include γ rays, β rays, electron beams, ultraviolet rays, visible rays, and infrared rays. Any known heat polymerization initiators and photo-polymerization initiators can be used for the polymerization initiator.

Specific examples of preferable radical polymerization initiators include (a) aromatic ketone compounds, (b) acylphosphine oxide compounds, (c) aromatic onium salt compounds, (d) organic peroxides, (e) thio compounds, (f) hexaaryl bisimidazole compounds, (g) ketoxime ester compounds, (h) borate compounds, (i) azinium compounds, (j) metallocene compounds, (k) active ester compounds, (l) compounds having a carbon-halogen bond, and (m) alkylamine compounds. These compounds can be used alone or in combination.

Specific examples of the radical polymerization initiators include benzophenone, Michler's ketone, 4,4'-bis(diethylamino)benzophenone, xanthone, thioxanthone, isopropyl xanthone, 2,4-diethylthioxanthone, 2-ethylanthraquinone, acetophenone, 2-hydroxy-2-methylpropiophenone, 2-hydroxy-2-methyl-4'-isopropylpropiophenone, 1-hydroxycyclohexyl phenyl ketone, isopropylbenzoin ether, isobutylbenzoin ether, 2,2-diethoxyacetophenone, 2,2-dimethoxy-2-phenylacetophenone, Camphorquinone, benzanthrone, 2-methyl-1-[4-(methylthio)phenyl]-2-morphorinopropane-1-one, 2-benzyl-2-dimethylamino-1-(4-morphorinophenyl) butanone-1, ethyl 4-dimethylaminobenzoate, isoamyl 4-dimethylaminobenzoate, 4,4'-di(t-butylperoxycarbonyl) benzophenone, 3,4,4'-tri(t-butylperoxycarbonyl) benzophenone, 3,3',4,4'-tetra(t-butylperoxycarbonyl) benzophenone, 3,3',4,4'-tetra(t-hexylperoxycarbonyl) benzophenone, 3,3'-di(methoxycarbonyl)-4,4'-di(t-butylperoxycarbonyl)benzophenone, 3,4'-di (methoxycarbonyl)-4,3'-di(t-butylperoxycarbonyl) benzophenone, 4,4'-di(methoxycarbonyl)-3,3'-di(t-butylperoxycarbonyl)benzophenone, 1,2-octanedione, 1-[4-(phenylthio)phenyl]-2-(o-benzoyloxime), 2-(4'-methoxystyryl)-4,6-bis(trichloromethyl)-s-triazine, 2-(3',4'-dimethoxystyryl)-4,6-bis(trichloromethyl)-s-triazine, 2-(2',4'-dimethoxystyryl)-4,6-bis(trichloromethyl)-s-triazine, 2-(2'-methoxystyryl)-4,6-bis(trichloromethyl)-s-triazine, 2-(4'-pentyloxystyryl)-4,6-bis(trichloromethyl)-s-triazine, 4-[p-N,N-di(ethoxycarbonylmethyl)]-2,6-di(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyryl)benzoxazole, 2-(p-dimethylaminostyryl)benzthiazole, 2-mercaptobenzothiazole, 3,3'-carbonylbis(7-diethylaminocoumarin), 2-(o-chlorophenyl)-4,4',5,5' tetraphenyl-1,2'-biimidazole, 2,2'-bis (2-chlorophenyl)-4,4',5,5'-tetrakis(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morphorinopropionyl)-9-n-dodecylcarbazole, 1-hydroxycyclohexyl phenyl ketone, bis(η5-2,4-cyclopentadiene-1-yl)-bis[2,6-difluoro-3-(1H-pyrole-1-yl)phenyl]titanium, bis(2,4,6-trimethylbenzoyl)phenylphosphine oxide, and 2,4,6-trimethylbenzoyldiphenylphosphine oxide.

Among these initiators, bis(2,4,6-trimethylbenzoyl)phenylphosphine oxide (IRGACURE 819 from BASF Japan Ltd.), 2,4,6-trimethylbenzoyldiphenylphosphine oxide (DAROCUR TPO from BASF Japan Ltd.), 1-hydroxycyclohexyl phenyl ketone (IRGACURE 184 from BASF Japan Ltd.), 2-methyl-[4-(methylthio)phenyl]-2-morphorinopropane-1-one (IRGACURE 907 from BASF Japan Ltd.), and 2-dimethylamino-2-(4-methylbenzyl)-1-(4-morphorine-4-ylphenyl)butane-1-one (IRGACURE 379 from BASF Japan) are preferable because they have good compatibility with other components included in the ink while being able to be cured with a small dose of ultraviolet rays.

The added amount of such a polymerization initiator is preferably from 1 to 50% by weight, more preferably from 2 to 40% by weight, and even more preferably from 5 to 30% by weight, based on the total weight of the polymerizable compound, and optional components included in the ink such as other polymerizable compounds mentioned later and colorants. In addition, the weight ratio (I/S) of such a polymerization initiator (I) to an optional sensitizer (S) mentioned later is preferably from 200/1 to 1/200, and more preferably from 50/1 to 1/50.

The content of a reactive monomer including such a polymerizable compound as mentioned above in the ink is preferably from 20 to 98% by weight, more preferably from 30 to 90% by weight, and even more preferably from 30 to 80% by weight. One or more polymerizable compounds can be used for the ink of this disclosure.

The ink of this disclosure can include other components to enhance properties of the ink as long as the components do not deteriorate the effect of this disclosure. Hereinafter, such ink components will be described.

The ink of this disclosure can include a colorant to form a color image. The colorant is not particularly limited, and one or more colorants are used for the ink while selected from any known colorants such as pigments, oil-soluble dyes, water-soluble dyes, and disperse dyes.

Among these colorants, pigments and oil-soluble dyes are preferable because of having a good combination of weather resistance and color reproducibility, and pigments are more preferable. It is preferable for the colorant to be included in the ink not to deteriorate the curing reactivity (polymerizability) of the ink when the ink is exposed to an active energy ray. Namely, it is preferable to use a colorant, which does not serve as a polymerization inhibitor (i.e., curing reaction inhibitor).

Among various pigments, one or more pigments are used for the ink while properly selected from the following organic and inorganic pigments having the below-mentioned color indexes depending on the purpose of the ink.

Specific examples of red or magenta pigments include Pigment Reds 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226 and 257, Pigment Violets 3, 19, 23, 29, 30, 37, 50 and 88, and Pigment Oranges 13, 16, 20 and 36.

Specific examples of blue or cyan pigments include Pigment Blues 1, 15, 15:1, 15:2, 15:3, 15:4, 15:6, 16, 17-1, 22, 27, 28, 29, 36 and 60.

Specific examples of green pigments include Pigment Greens 7, 26, 36 and 50.

Specific examples of yellow pigments include Pigment Yellows 1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185 and 193.

Specific examples of black pigments include Pigment blacks 7, 28 and 26.

Specific examples of white pigments include Pigment whites 6, 18 and 21.

Next, oil-soluble dye materials for use in the ink of this disclosure will be described. In this disclosure, an oil-soluble dye is defined as a dye which is substantially insoluble in water. Specifically, the solubility of such an oil-soluble dye material in 100 g of water at 25° C. is not greater than 1 g, preferably not greater than 0.5 g, and more preferably not greater than 0.1 g. Namely, oil-soluble dye materials mean water-insoluble pigments and oil-soluble dyes. Among these materials, oil-soluble dyes are preferable.

Specific examples of yellow oil-soluble dyes include aryl- or hetaryl-azo dyes, which have a coupling component selected from phenol compounds, naphthol compounds, aniline compounds, pyrazolone compounds, pyridine compounds, and closed-type active methylene compounds; azo methine dyes, which have a coupling component selected from closed-type active methylene compounds; methine dyes such as benzylidene dyes and monomethine oxonol dyes; quinone dyes such as naphthoquinone dyes and anthraquinone dyes; quinophthalone dyes, nitro or nitroso dyes, acridine dyes, and acridinone dyes.

Specific examples of magenta oil-soluble dyes include aryl- or hetaryl-azo dyes, which have a coupling component selected from phenol compounds, naphthol compounds, and aniline compounds; azomethine dyes, which have a coupling component selected from pyrazolone compounds, and pyrazolonetriazole compounds; methine dyes such as allylidene dyes, styryl dyes, merocyanine dyes, and oxonol dyes; carbonium dyes such as diphenyl methane dyes, triphenyl methane dyes, and xanthene dyes; quinone dyes such as naphthoquinone, anthraquinone dyes, and anthrapyridone dyes; and dioxadine dyes.

Specific examples of cyan oil-soluble dyes include indoaniline dyes, indophenol dyes, azomethine dyes which have a coupling component selected from pyrrolotriazole compounds; polymethine dyes such as cyanine dyes, oxonol dyes, and morocyanine dyes; carbonium dyes such as diphenylmethane dyes, triphenyl methane dyes, and xanthene dyes; phthalocyanine dyes, anthraquinone dyes, aryl- or hetaryl-azo dyes, which have a coupling component selected from phenol compounds, naphthol compounds, and aniline compounds, and indigo or thioindigo dyes.

Specific examples of oil-soluble dyes include C.I. Solvent Blacks 3, 7, 27, 29 and 34, C.I. Solvent yellows 14, 16, 19, 29, 30, 56, 82, 93 and 162, C.I. Solvent reds 1, 3, 8, 18, 24, 27, 43, 49, 51, 72, 73, 109, 122, 132 and 218, C.I. Solvent Violet 3, C.I. Solvent Blues 2, 11, 25, 35, 38, 67 and 70, C.I. Solvent Greens 3 and 7, and C.I. Solvent Orange 2.

Disperse dyes can be used for the ink of this disclosure as long as the disperse dyes can be dissolved in a water-incompatible organic solvent. Specific examples thereof include C.I. Disperse Yellows 5, 42, 54, 64, 79, 82, 83, 93, 99, 100, 119, 122, 124, 126, 160, 184:1, 186, 198, 199, 201, 204, 224 and 237, C.I. Disperse Oranges 13, 29, 31:1, 33, 49, 54, 55, 66, 73, 118, 119 and 163, C.I. Disperse Reds 54, 60, 72, 73, 86, 88, 91, 92, 93, 111, 126, 127, 134, 135, 143, 145, 152, 153, 154, 159, 164, 167:1, 177, 181, 204, 206, 207, 221, 239, 240, 258, 277, 278, 283, 311, 323, 343, 348, 356 and 362, C.I. Disperse Violet 33, C.I. Disperse Blues 56, 60, 73, 87, 113, 128, 143, 148, 154, 158, 165, 165:1, 165:2, 176, 183, 185, 197, 198, 201, 214, 224, 225, 257, 266, 267, 287, 354, 358, 365 and 368, and C.I. Disperse Greens 6:1 and 9.

It is preferable that a colorant is dispersed properly in the ink. Specific examples of the dispersing device to disperse a colorant in the ink include ball mills, sand mills, ring mills, attritors, roll mills, agitators, HENSCHEL MIXERs, colloid mills, supersonic homogenizers, pearl mills, wet jet mills, and paint shakers.

When a colorant is dispersed, a dispersant can be used. The dispersant is not particularly limited, but polymer dispersants are preferable. The added amount of a dispersant is from 1 to 50 parts by weight based on 100 parts by weight of the colorant used.

The ink of this disclosure can include one or more colorants depending on the purpose of the ink.

When a colorant is present as a solid in the ink, the average particle diameter of the colorant in the ink is preferably from 0.005 μm to 0.5 μm, more preferably from 0.01 μm to 0.45 μm, and even more preferably from 0.015 μm to 0.4 μm. The average particle diameter of a colorant in the ink can be adjusted by selecting a proper colorant, a proper dispersant, and a proper dispersing medium while properly determining the dispersing conditions and filtering conditions. By thus controlling the average particle diameter, occurrence of a nozzle clogging problem such that nozzles from which the ink is ejected as droplets are clogged with particles of the colorant included in the ink can be prevented and the ink can maintain a good combination of preservation stability, transparency and curing sensitivity.

The content of a colorant in the ink is determined depending on the purpose of the ink, and is generally from 0.5 to 10% by weight, and preferably from 1 to 8% by weight, from the viewpoints of physical properties and coloring property of the ink. When a white pigment such as titanium oxide is used as a colorant, the content of such a white pigment is preferably from 5 to 30% by weight, and more preferably from 10 to 25% by weight, based on the total weight of the ink in order that the ink has a good shielding property.

Next, polymerizable compounds (monomers) (hereinafter referred to as optional polymerizable compounds) other than the polymerizable compounds mentioned above will be described.

The ink of this disclosure can optionally include a polymerizable compound other than the polymerizable compounds mentioned above (hereinafter sometimes referred to as an essential polymerizable compound). The added amount of such an optional polymerizable compound is from 0.01 to 100 parts by weight, and preferably from 0.1 to 50 parts by weight, based on 1 part by weight of the essential polymerizable compound included in the ink. Suitable compounds for use as such optional polymerizable compounds include radically polymerizable compounds, cationically polymerizable compounds, and anionically polymerizable compounds.

Radically polymerizable compounds are compounds such as monomers, oligomers and polymers, which include at least one radically polymerizable ethylenic unsaturated bond in a molecule thereof. These radically polymerizable compounds can be used alone or in combination to enhance the targeted properties of the ink.

Specific examples of such radically polymerizable compounds include unsaturated carboxylic acids such as acrylic acid, methacrylic acid, itaconic acid, crotonic acid, isocrotonic acid and maleic acid, and salts and derivatives thereof; anhydrides having an ethylenic unsaturated group, acrylonitrile, styrene, unsaturated polyesters, unsaturated polyethers, unsaturated polyamides, and unsaturated urethanes.

Specific examples of (meth)acrylic acid derivatives for use as optional polymerizable compounds include acrylic acid derivatives such as 2-hydroxyethyl acrylate, butoxyethyl acrylate, carbitol acrylate, cyclohexyl acrylate, tetrahydrofurfuryl acrylate, benzyl acrylate, bis(4-acryloxypolyethoxyphenyl)propane, neopentyl glycol diacrylate, ethoxylated neopentyl glycol diacrylate, propoxylated neopentyl glycol diacrylate, 1,6-hexanediol diacrylate, ethylene glycol diacrylate, diethylene glycol diacrylate, diethylene glycol diacrylate, tetraethylene glycol diacrylate, polyethylene glycol diacrylate, propylene glycol diacrylate, dipropylene glycol diacrylate, tripropylene glycol diacrylate, tetrapropylene glycol diacrylate, polypropylene glycol diacrylate, pentaerythritol triacrylate, pentaerythritol tetraacrylate, dipentaerythritol tetraacrylate, trimethylol propane triacrylate, tetramethylol methane tetraacrylate, oligoester acrylate, and epoxy acrylate; and methacrylic acid derivatives such as methyl methacrylate, n-butyl methacrylate, allyl methacrylate, glycidyl methacrylate, benzyl methacrylate, dimethylaminomethyl methacrylate, 1,6-hexanediol dimethacrylate, ethylene glycol dimethacrylate, triethylene glycol dimethacrylate, polyethylene glycol dimethacrylate, polypropylene glycol dimethacrylate, trimethylolethane trimethacrylate, trimethylolpropane trimethacrylate, and 2,2-bis(4-methacryloxypolyethoxyphenyl)propane.

Specific examples of acrylamide derivatives include N-methylol acrylamide, diacetone acrylamide, 2-hydroxyethyl acrylamide, and acryloyl morphorine.

Specific examples of allyl compound derivatives include allyl glycidyl ether, diallyl phthalate, and triallyl trimellitate.

In addition, the marketed products, reactive monomers, oligomers, and polymers described in the body and supporting data such as photo-reactive material data of OPTICAL APPLICATION TECHNOLOGY AND MATERIAL DICTIONARY published in Japan in 2006 by Industrial Technology Service Center can also be used. Specific examples thereof include acrylic acid ester compounds such as 2-acryloyloxyethyl phthalate, 2-acryloyloxyethyl-2-hydroxyethylphthalate, 2-acryloyloxyethyl hexahydrophthalate, 2-acryloyloxypropyl phthalate, 2-ethyl-2-butyl-propanediol acrylate, 2-ethylhexyl acrylate, 2-ethylhexyl carbitol acrylate, 2-hydroxybutyl acrylate, 2-hydroxyethyl acrylate, and 2-hydroxypropyl acrylate; and methacrylic acid ester compounds such as 1,3-butylene glycol dimethacrylate, 2-ethylhexyl methacrylate, 2-hydroxy-3-acryloyloxypropyl methacrylate, 2-hydroxy-3-methacryloxypropyl trimethylammonium chloride, 2-hydroxybutyl methacrylate, 2-hydroxyethyl methacrylate, 2-hydroxypropyl methacrylate, 3-chloro-2-hydroxypropyl methacrylate, alkyl(C12-13) methacrylate, and alkyl(C12-15) methacrylate. In addition, ethylene oxide adduct of trimethylolpropane triacrylate, 1,9-nonanediol diacrylate, isobonyl acrylate, N-vinylformamide, triallylisocyanurate, the above-mentioned anionic, cationic and nonionic oligomers, which are described in OPTICAL APPLICATION TECHNOLOGY AND MATERIAL DICTIONARY can also be used.

In addition, vinyl ether compounds can also be used as optional radically polymerizable compounds. Specific examples thereof include di- or tri-vinyl ether compounds such as ethylene glycol divinyl ether, diethylene glycol divinyl ether, triethylene glycol divinyl ether, propylene glycol divinyl ether, dipropylene glycol divinyl ether, butanediol divinyl ether, hexanediol divinyl ether, cyclohexanedimethanol divinyl ether, and trimethylol propane trivinyl ether; and monovinyl ether compounds such as ethylene glycol monvinyl ether, triethylene glycol monovinyl ether, hydroxyethyl monovinyl ether, hydroxynonyl monovinyl ether, ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexanedimethanol monovinyl ether, n-propyl vinyl ether, isopropyl vinyl ether, isopropenyl-o-propylene carbonate, dodecyl vinyl ether, diethylene glycol monovinyl ether, and octadecyl vinyl ether.

In addition, vinyl ether compounds described in the body and supporting data such as photo-reactive material data of OPTICAL APPLICATION TECHNOLOGY AND MATERIAL DICTIONARY published in Japan in 2006 by Industrial Technology Service Center (Japan) can also be used. Specific examples thereof include butanediol-1,4-divinyl ether, methyl vinyl ether, propyl vinyl ether, and vinyl-4-hydroxybuyl ether. These vinyl ether compounds can be used alone or in combination.

Other polymerizable compounds such as (meth)acrylic monomer or prepolymers, epoxy monomers or prepolymers, and urethane monomers or prepolymers can also be used for the ink.

Specific examples thereof include 2-ethylhexyl diglycol acrylate, 2-hydroxy-3-phenoxypropyl acrylate, 2-hydroxybutyl acrylate, acrylate of neopentyl glycol hydroxypivalate, 2-acryloyloxyethyl phthalate, methoxypolyethylene glycol acrylate, tetramethylol methane triacrylate, 2-acryloyloxyethyl-2-hydroxyethyl phthalate, dimethylol tricyclodecane diacrylate, ethoxylated phenyl acrylate, 2-acryloyloxyethyl succinate, acrylate of ethylene oxide adduct of nonyl phenol, modified glycerin triacrylate, acrylic acid adduct of bisphenol A diglycidyl ether, modified bisphenol A diacrylate, phenoxypolyethylene glycol acrylate, 2-acryloyloxyethyl hexahydrophthalate, diacrylate of propylene oxide adduct of bisphenol A, diacrylate of ethylene oxide adduct of bisphenol A, dipentaerythritol hexaacrylate, pentaerythritol triacrylate, tolylene diisocyanate urethane prepolymer, lactone-modified flexible acrylate, lactone-modified acrylate, butoxyethyl acrylate, acrylic acid adduct of propylene glycol diglycidyl ether, hexamethylene diisocyanate urethane prepolymer, 2-hydroxyethyl acrylate, methoxydipropylene glycol acrylate, di(trimethylol)propane tetraacrylate, stearyl acrylate, isoamyl acrylate, isomyristyl acrylate, and isostearyl acrylate.

In addition to inks using the combination of a radically polymerizable compound and a radical polymerization initiator mentioned above, radical/cationic hybrid type curable inks using the combination of a radically polymerizable compound and a radical polymerization initiator and a combination of cationically polymerizable compound and a cationic polymerization initiator, and radical/anionic hybrid type curable inks using the combination of a radically polymerizable compound and a radical polymerization initiator and a combination of anionically polymerizable compound and an anionic polymerization initiator can also be used in this disclosure.

The cationically polymerizable compound is not particularly limited as long as the compound starts a polymerization reaction based on an acid generated by a photo acid generator and cures, and any known cationically polymerizable monomers, which are known as cationically photo-polymerizable monomers, can be used. For example, various epoxy compounds, vinyl ether compounds, and oxetane compounds, which are described in OPTICAL APPLICATION TECHNOLOGY AND MATERIAL DICTIONARY published in Japan in 2006 by Industrial Technology Service Center (Japan), such as bis(3-ethyl-3-oxetanylmethyl)ether, and CELLOXIDE 2021 (difunctional alicyclic epoxy compound) from DAICEL CORP. can be used as cationically polymerizable compounds. Any known cationic polymerization initiators (i.e., photo acid generators) can be used in combination with such cationically polymerizable compounds. Specific examples thereof include salts (e.g., $B(C_6F_5)_4^-$, $PF_6^-$, $AsF_6^-$, $SbF_6^-$ or $CF_3SO_3^-$) of aromatic onium compounds such as diazonium, ammonium, iodonium, sulfonium and phosphonium compounds; sulfonated compounds capable of generating sulfonic acid, halogenated compounds capable of generating halogenated hydrogen when being exposed to light, and iron-arene complexes. These cationic polymerization initiators can be used alone or in combination.

Various epoxy compounds, lactone compounds, acrylic compounds, and methacrylic compounds can be used as anionically polymerizable compounds. Among these anionically polymerizable compounds, acrylic compounds, and methacrylic compounds, which are exemplified above as radically polymerizable compounds, are preferable. Any known anionic polymerization initiators (i.e., photo base generators) can be used in combination with such anionically polymerizable compounds. Specific examples of the anionic polymerization initiators include orthonitrobenzyl carbamate derivatives, orthoacyloxyl derivatives, and orthocarbamoyl oxime amidine derivatives.

The ink of this disclosure can optionally include a sensitizer to accelerate decomposition of a polymerization initiator when the initiator is exposed to an active energy ray. In this application, the sensitizer is defined as a material capable of achieving an electronically excited state by absorbing a specific active energy ray. When a sensitizer achieving an electronically excited state is contacted with a polymerization initiator, an action such as electron transfer, energy transfer, and heat generation is caused, thereby accelerating the chemical change of the polymerization initiator (e.g., decomposition, or formation of a radical, an acid or a base). It is preferable to choose a proper sensitizer depending on the wavelength of an active energy ray used for allowing the polymerization initiator to generate a polymerization starting material. Sensitizing dyes are preferably used as the sensitizer, and the below-mentioned sensitizing dyes, which absorb light with a wavelength of from 350 nm to 450 nm, can be preferably used.

Specific examples of such sensitizing dyes include polynuclear aromatic compounds (e.g., pyrene, perylene and triphenylene), xanthene compounds (e.g., fluorescein, eosin, erythrosine, Rhodamine B and Rose Bengal), cyanine compounds (e.g., thiacarbocyanine, and oxacarbocyanine), merocyanine compounds (e.g., merocyanine and carbomerocyanine), thiazine compounds (e.g., thionine, Methylene Blue and Toluidine Blue), acridine compounds (e.g., acridine orange, chloroflavin and acriflavin), anthraquinone compounds (e.g., anthaquinone), squarylium compounds (e.g., squarylium), and coumarin compounds (e.g., 7-diethylamino-4-methylcoumarin).

The ink of this disclosure can include a cosensitizer, which can enhance the sensitivity of a sensitizing dye to an active energy ray and/or which can prevent inhibition of polymerization of a polymerizable compound due to oxygen. Specific examples of such a cosensitizer include amine compounds such as triethanolamine, ethyl p-dimethylaminobenzoate, p-formyldimethylaniline, and p-methylthiodimethylaniline; and thiols and sulfides such as 2-mercaptobenzothiazole, 2-mercaptobenzoxazole, 2-mercaptobenzimidazole, 2-mercapto-4(3H)-quinazoline, and β-mercaptonaphthalene.

The ink of this disclosure can further include other components such as polymerization inhibitors and solvents. A polymerization inhibitor is added to enhance the preservability (preservation stability) of the ink. In addition, the ink of this disclosure can be ejected while heated to decrease the viscosity thereof. In this case, it is preferable to add such a polymerization inhibitor to the ink to prevent occurrence of a problem in that the nozzles ejecting the ink as droplets are clogged with a heat-polymerized material of the ink.

Specific examples of such a polymerization inhibitor include hydroquinone, methylhydroquinone, benzoquinone, p-methoxyphenol, TEMPO (2,2,6,6-tetramethylpiperidine-1-oxyl), TEMPOL (2,2,6,6-tetramethypiperidinol-N-oxyl), and cupferron Al complexes. The added amount of such a polymerization inhibitor is preferably from 200 to 20,000 ppm based on the total weight of the ink.

The viscosity of the ink of this disclosure is preferably from 7 to 30 mPa·s, and more preferably from 7 to 25 mPa·s in a use environment, from the viewpoint of ejection stability of the ink in inkjet recording apparatus.

It is preferable for the ink of this disclosure not to include a solvent. However, in order to enhance properties of the ink such as adhesion of the ink to recording media after curing of the ink, a solvent such as organic solvents and water can be included in the ink as long as the solvent does not deteriorate the curing speed and other properties of the ink. The added amount of such a solvent in the ink is from 0.1 to 5% by weight, and preferably from 0.1 to 3% by weight, based on the total weight of the ink.

In addition, the ink can further include known additives such as surfactants, leveling agents, malting agents, and ink film property adjusting agents (such as polyester resins, polyurethane resins, vinyl resins, acrylic resins, rubbers and waxes). Further, the ink can include a tackifier, which does not inhibit polymerization of the ink, to improve adhesion of the ink to polyolefin and PET (polyethylene tetraphthalate).

Next, the ink cartridge of this disclosure will be described.

The ink cartridge of this disclosure includes the above-mentioned ink, which is contained in a container. By using such an ink cartridge, contact of fingers with the ink can be avoided in an ink change operation, thereby preventing fingers and cloths from being contaminated with the ink. In addition, inclusion of a foreign material into the ink can be prevented.

The container is not particularly limited, and the shape, structure, size and constitutional material are properly determined depending on the purpose of the ink cartridge. Specifically, an ink cartridge having an ink bag formed of a material having little air permeability such as aluminum-laminated films and resin films can be used.

The ink cartridge of this disclosure will be described by reference to FIG. 1.

FIG. 1 is a schematic view illustrating an ink bag 11 for use in the ink cartridge of this disclosure. The ink bag 11 includes an inlet 12 from which the ink is injected into the ink bag 11, and an outlet 13 through which the ink is supplied to an inkjet recording apparatus. When the ink is contained in the ink bag 11, the ink is injected into the ink bag 11 from the inlet 12. After discharging air from the ink bag 11, the inlet 12 is closed by welding or the like. When the ink bag 11 is used, the ink bag is set to an inkjet recording apparatus in such a manner that a needle of the inkjet recording apparatus is inserted into an ink outlet 13 of the ink bag 11, and thereby the ink in the ink bag 11 can be supplied to the inkjet recording apparatus. The outlet 13 is made of a rubber or the like.

Figure 2:
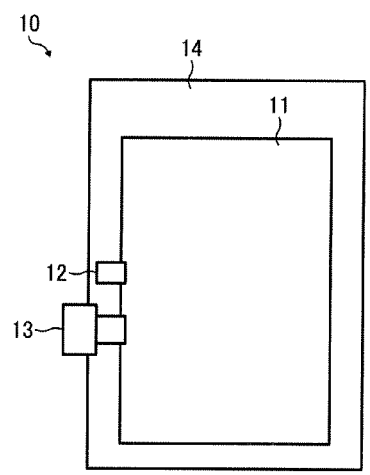
FIG. 2 is a schematic view illustrating an ink cartridge including the ink bag illustrated in FIG. 1.

As mentioned above, the ink bag 11 is typically made of a material having little air permeability such as aluminum-laminated films. As illustrated in FIG. 2, the ink bag 11 is typically contained in a cartridge case 14, which is typically made of a plastic, to form an ink cartridge 10. The ink cartridge 10 is detachably attached to an inkjet recording apparatus. By using such an ink cartridge for an inkjet recording apparatus, the ink exchanging or replenishing operation can be easily performed, resulting in enhancement of the workability in the operation.

Next, the inkjet recording apparatus of this disclosure will be described.

The inkjet recording apparatus of this disclosure includes the above-mentioned ink cartridge of this disclosure, and an inkjet recording device to eject droplets of the inkjet ink in the ink cartridge to form an image on a recording medium. Specific examples of the inkjet recording methods include continuous ink ejecting methods, and on demand recording methods such as piezoelectric methods, thermal methods and electrostatic methods.

The inkjet recording apparatus of this disclosure will be described in detail by reference to FIG. 3.

Figure 3:
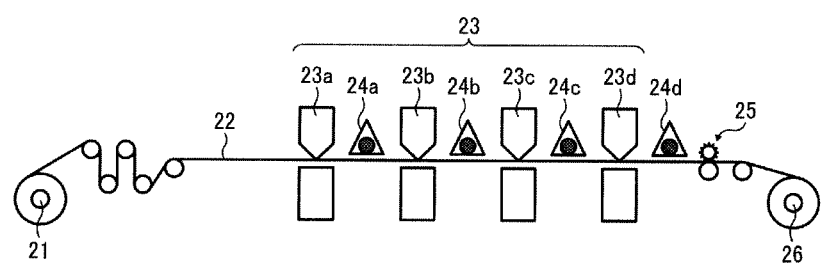
FIG. 3 is a schematic view illustrating an inkjet recording apparatus according to an embodiment.

FIG. 3 is a schematic view for describing the image recording mechanism of the inkjet recording apparatus of this disclosure.

An inkjet recording apparatus illustrated in FIG. 3 includes an inkjet recording device 23 including a yellow inkjet recording head 23a, a magenta inkjet recording head 23b, a cyan inkjet recording head 23c and a black inkjet recording head 23d to respectively eject yellow, magenta, cyan and black inks, each of which is the curable ink of this disclosure, to form yellow, magenta, cyan and black color images on a recording medium 22 fed from a roll-form recording medium 21; and ultraviolet light sources 24a, 24b, 24c and 24d serving as active energy ray irradiators to irradiate the yellow, magenta, cyan and black color images with an active energy ray (such as ultraviolet light) to cure the color images. In this inkjet recording apparatus illustrated in FIG. 3, an ultraviolet crosslinking operation is performed after every image forming operation. After the recording medium 22 bearing cured color images thereon is processed by a processor (such as a perforating device) 25, the recording medium 22 is wound as a roll-form print 26.

Each of the recording heads 23a-23d can have a heater to heat the inkjet ink in the ink ejecting portion of the heads, so that the ink can be satisfactorily liquefied (i.e., the ink can have a proper viscosity).

When the former recorded image has a large image area proportion or the former image is recorded at a high speed, the temperature of the recording medium 22 often increases. In order to prevent increase in temperature of the recording medium 22, a cooler to cool the recording medium to about room temperature can be provided in such a manner that the cooler faces the upper or lower surface of the recording medium 22 or is contacted with the upper or lower surface.

Specific examples of the recording medium 22 include paper, films, metals, and complex materials thereof. The recording medium 22 has a roll form in the inkjet recording apparatus illustrated in FIG. 3, but the shape of the recording medium 22 is not limited thereto. Recording media having a sheet form or the like can also be used. In the inkjet recording apparatus illustrated in FIG. 3, images are formed on one side of the recording medium 22, but the inkjet recording apparatus of this disclosure is not limited thereto. The inkjet recording apparatus may have such a configuration as to form images on both sides of the recording medium 22.

When high speed image formation is performed, it is preferable to perform an ultraviolet curing operation after every image forming operation, so that images with a better curing property can be formed. However, it is possible that the ultraviolet light sources 24a, 24b and 24c are mildly operated or are not operated, and the light source 24d is operated so as to irradiate the recorded images with a sufficient amount of ultraviolet light. By using this method, energy saving and cost saving can be made.

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

The inks in the following examples do not include additives such as colorants to clarify the effect of the polymerizable compound of this disclosure.

Synthesis Example 1

Synthesis of the Above-Mentioned Polymerizable Compound F-2

Initially, 7.8 g (80 mmol) of diallylamine was added to 70 ml of dehydrated dichloromethane contained in a flask. After air in the flask was replaced with an argon gas, 11.6 g (115 mmol) of triethylamine was fed to the flask. After the mixture was cooled to about –10° C., 8.7 g (96 mmol) of acrylic acid chloride was gradually dropped into the flask so that the temperature of the system in the flask fell in a range of from –10 to –5° C., followed by agitation of the mixture for 2 hours at room temperature. After the precipitate was removed from the product by filtering, the filtrate was washed with water, followed by washing with a saturated aqueous solution of sodium hydrogen carbonate, and washing with a saturated aqueous solution of sodium chloride. After the washed product was dried using sodium sulfate, the product was condensed under a reduced pressure. Thus, a brown oily material was obtained. The oily material was refined by column chromatography (using 250 g of WAKOGEL C300 from Wako Pure Chemical industries, Ltd.). Thus, 6.4 g of a pale yellow oily material was obtained. It was confirmed from $^1$H-NMR and IR spectroscopy mentioned below that the pale yellow oily material is the compound F-2 mentioned above. The yield of the product was about 53%.

$^1$H-NMR (using CDCl$_3$): δ 3.89 (s, 2H), 3.99 (d, 2H), 5.09 (d, 1H), 5.12 (d, 2H), 5.17 (d, 1H), 5.63 (dd, 1H), 5.69-5.79 (m, 2H), 6.31 (dd, 1H), and 6.41-6.49 (m, 1H).

IR (using NaCl): 3083, 3012, 2984, 2921, 1652, 1615, 1465, 1439, 1416, 1360, 1277, 1224, 1194, 1138, 1059, 980, 957, 925, 795, 653 and 559 cm$^{-1}$.

Synthesis Example 2

Synthesis of the Above-Mentioned Polymerizable Compound A-3

Initially, 8.1 g (70 mmol) of N-(2-hydroxyethyl)acrylamide (reagent from Tokyo Kasei Kogyo Co., Ltd.) was added to 70 ml of dehydrated dichloromethane contained in a flask.

After air in the flask was replaced with an argon gas, 10.1 g (100 mmol) of triethylamine was fed to the flask. After the mixture was cooled to about −10° C., 7.6 g (84 mmol) of acrylic acid chloride was gradually dropped into the flask so that the temperature of the system in the flask fell in a range of from −10 to −5° C., followed by agitation of the mixture for 2 hours at room temperature. After the precipitate was removed from the product by filtering, the filtrate was washed with water, followed by washing with a saturated aqueous solution of sodium hydrogen carbonate, and washing with a saturated aqueous solution of sodium chloride. After the washed product was dried using sodium sulfate, the product was condensed under a reduced pressure. Thus, a brown oily material was obtained. The oily material was refined by column chromatography (using 250 g of WAKOGEL C300 from Wako Pure Chemical industries, Ltd.). Thus, 7.8 g of a colorless oily material was obtained. It was confirmed from $^1$H-NMR and IR spectroscopy mentioned below that the colorless oily material is the compound A-3 mentioned above. The yield of the product was about 66%.

$^1$H-NMR (using CDCl$_3$): δ 3.57-3.62 (m, 214), 4.22-4.27 (m, 2H), 5.61 (d, 1H), 5.83 (d, 1H), 6.04-6.14 (m, 2H), 6.24 (d, 1H), 6.39 (d, 114), and 6.38-6.52 (br, 1H).

IR (using NaCl): 3285, 3074, 2958, 1727, 1660, 1629, 1548, 1408, 1296, 1272, 1246, 1190, 1126, 1068, 1036, 984, 901, 809 and 668 cm$^{-1}$.

Synthesis Example 3

Synthesis of the Above-Mentioned Polymerizable Compound A-4

Initially, 13.0 g (113 mmol) of N-(2-hydroxyethyl)acrylamide (reagent from Tokyo Kasei Kogyo Co., Ltd.) was added to 70 ml of dehydrated dichloromethane contained in a flask. After air in the flask was replaced with an argon gas, 17.2 g (170 mmol) of triethylamine was fed to the flask. After the mixture was cooled to about −10° C., 14.6 g (140 mmol) of acrylic acid chloride was gradually dropped into the flask so that the temperature of the system in the flask fell in a range of from −10 to −5° C., followed by agitation of the mixture for 2 hours at room temperature. After the precipitate was removed from the product by filtering, the filtrate was washed with water, followed by washing with a saturated aqueous solution of sodium hydrogen carbonate, and washing with a saturated aqueous solution of sodium chloride. After the washed product was dried using sodium sulfate, the product was condensed under a reduced pressure. Thus, a brown oily material was obtained. The oily material was refined by column chromatography (using 500 g of WAKOGEL C300 from Wako Pure Chemical industries, Ltd.). Thus, 13.0 g of a colorless oily material was obtained. It was confirmed from $^1$H-NMR and IR spectroscopy mentioned below that the colorless oily material is the compound A-4 mentioned above. The yield of the product was about 66%.

$^1$H-NMR (using CDCl$_3$): δ 1.95 (dd, 3H), 3.65 (t, 2H), 4.29 (t, 2H), 5.58-5.62 (m, 1H), 5.63-5.68 (m, 1H), 6.10-6.16 (m, 2H), 6.18-6.28 (br, 1H), 6.25-6.23 (m, 1H), and 6.23-6.32 (m, 1H).

IR (using NaCl): 3290, 3078, 2959, 1719, 1661, 1628, 1558, 1541, 1507, 1456, 1407, 1375, 1320, 1297, 1245, 1166, 1041, 986, 955 and 814 cm$^{-1}$.

Synthesis Example 4

Synthesis of the Above-Mentioned Polymerizable Compound C-5

Initially, 15.0 g (200 mmol) of 2-(methylamino)ethanol (reagent from Tokyo Kasei Kogyo Co., Ltd.) was added to 170 ml of dehydrated dichloromethane contained in a flask. After air in the flask was replaced with an argon gas, 24.3 g (240 mmol) of triethylamine was fed to the flask. After the mixture was cooled to about −10° C., 18.1 g (200 mmol) of acrylic acid chloride was gradually dropped into the flask so that the temperature of the system in the flask fell in a range of from −10 to −5° C., followed by agitation of the mixture for 2 hours at room temperature. After the precipitate was removed from the product by filtering, the filtrate was condensed, and 200 ml of ethyl acetate was added to the condensed filtrate, followed by agitation at room temperature. A yellow oily material, which was obtained by condensing the ethyl acetate solution, was refined by column chromatography (using 300 g of WAKOGEL 0300 from Wako Pure Chemical industries, Ltd.). Thus, 7.9 g of a colorless oily material was obtained. It was confirmed from $^1$H-NMR and IR spectroscopy mentioned below that the colorless oily material is the compound C-5 mentioned above. The yield of the product was about 30%.

$^1$H-NMR (using CDCl$_3$): δ 3.05 (s, 1.5H), 3.15 (s, 1.5H), 3.69 (t, 1H), 3.74 (t, 1H), 4.30 (t, 1H), 4.36 (t, 1H), 5.67-5.73 (m, 1H), 5.83-5.88 (m, 1H), 6.05-6.16 (m, 1H), 6.30-6.44 (m, 1H), and 6.54-6.65 (m, 1H).

IR (using NaCl): 2957, 1726, 1651, 1614, 1451, 1409, 1376, 1295, 1271, 1189, 1137, 1062, 982, 810, 795, 751, 667 and 604 cm$^{-1}$ Synthesis Example 5

Synthesis of the Above-Mentioned Polymerizable Compound C-6

Initially, 8.3 g (110 mmol) of 2-(methylamino)ethanol (reagent from Tokyo Kasei Kogyo Co., Ltd.) was added to 170 ml of dehydrated dichloromethane contained in a flask. After air in the flask was replaced with an argon gas, 24.3 g (240 mmol) of triethylamine was fed to the flask. After the mixture was cooled to about −10° C., 9.1 g (100 mmol) of acrylic acid chloride was gradually dropped into the flask so that the temperature of the system in the flask fell in a range of from −10 to −5° C., followed by agitation of the mixture for 2 hours at room temperature. After the reaction product was cooled to about −10° C., 10.5 g (100 mmol) of methacrylic acid chloride was gradually dropped into the flask so that the temperature in the flask fell in a range of from −10 to −5° C., followed by agitation of the mixture for 2 hours at room temperature. After the precipitate was removed from the product by filtering, the filtrate was washed with water, followed by washing with a saturated aqueous solution of sodium hydrogen carbonate, and washing with a saturated aqueous solution of sodium chloride. After the washed product was dried using sodium sulfate, the product was condensed under a reduced pressure. Thus, a brown oily material was obtained. The oily material was refined by column chromatography (using 500 g of WAKOGEL C300 from Wako Pure Chemical industries, Ltd.). Thus, 5.2 g of a pale yellow oily material was obtained. It was confirmed from $^1$H-NMR and IR spectroscopy mentioned below that the pale yellow oily material is the compound C-6 mentioned above. The yield of the product was about 26%.

$^1$H-NMR (using CDCl$_3$): δ 1.93 (s, 1.5H), 1.94 (s, 1.5H), 3.06 (s, 1.5H), 3.16 (s, 1.5H), 3.70 (t, 1H), 3.75 (t, 1H), 4.29 (t, 1H), 4.34 (t, 1H), 5.57-5.61 (m, 1H), 5.67-5.73 (m, 1H), 6.10 (d, 1H), 6.30-6.38 (m, 1H), and 6.55-6.66 (m, 1H).

IR (using NaCl): 2958, 1720, 1651, 1615, 1453, 1416, 1377, 1313, 1296, 1164, 1036, 981, 953, 815 and 795 cm$^{-1}$.

Synthesis Example 6

Synthesis of the Above-Mentioned Polymerizable Compound C-16

Initially, 13.0 g (70 mmol) of 2-(t-buylamino)ethyl methacrylate (reagent from Polysciences, Inc.) was added to 100 ml of dehydrated dichloromethane contained in a flask. After air in the flask was replaced with an argon gas, 10.1 g (100 mmol) of triethylamine was fed to the flask. After the mixture was cooled to about −10° C., 7.6 g (84 mmol) of acrylic acid chloride was gradually dropped into the flask so that the temperature of the system in the flask fell in a range of from −10 to −5° C., followed by agitation of the mixture for 2 hours at room temperature. After the precipitate was removed from the product by filtering, the filtrate was washed with water, followed by washing with a saturated aqueous solution of sodium hydrogen carbonate, and washing with a saturated aqueous solution of sodium chloride. After the washed product was dried using sodium sulfate, the product was condensed under a reduced pressure. Thus, a brown oily material was obtained. The oily material was refined by column chromatography (using 300 g of WAKOGEL C300 from Wako Pure Chemical industries, Ltd.). Thus, 13.7 g of a pale yellow oily material was obtained. It was confirmed from $^1$H-NMR and IR spectroscopy mentioned below that the pale yellow oily material is the compound C-16 mentioned above. The yield of the product was about 80%.

$^1$H-NMR (using CDCl$_3$): δ 1.50 (s, 94H), 1.94 (s, 3H), 3.69 (t, 2H), 4.23 (t, 2H), 5.59-5.64 (m, 2H), 6.10-6.13 (m, 1H), 6.23-6.28 (m, 1H), and 6.65-6.72 (m, 1H).

IR (using NaCl): 2964, 2929, 1720, 1652, 1614, 1453, 1415, 1362, 1317, 1295, 1251, 1220, 1200, 1161, 1104, 1040, 981, 947, 814, 798, 655 and 603 cm$^{-1}$ Synthesis Example 7

Synthesis of the Above-Mentioned Polymerizable Compound D-12

Initially, 11.9 g (53 mmol) of 2,2,4,4-tetramethyl-4-piperidyl methacrylate (reagent from Tokyo Kasei Kogyo Co., Ltd.) was added to 100 ml of dehydrated dichloromethane contained in a flask. After air in the flask was replaced with an argon gas, 7.8 g (77 mmol) of triethylamine was fed to the flask. After the mixture was cooled to about −10° C., 5.8 g (77 mmol) of acrylic acid chloride was gradually dropped into the flask so that the temperature of the system in the flask fell in a range of from −10 to −5° C., followed by agitation of the mixture for 2 hours at room temperature. After the precipitate was removed from the product by filtering, the filtrate was washed with water, followed by washing with a saturated aqueous solution of sodium hydrogen carbonate, and washing with a saturated aqueous solution of sodium chloride. After the washed product was dried using sodium sulfate, the product was condensed under a reduced pressure. Thus, a brown oily material was obtained. The oily material was refined by column chromatography (using 300 g of WAKOGEL C300 from Wako Pure Chemical industries, Ltd.). Thus, 12.4 g of a pale yellow oily material was obtained. It was confirmed from $^1$H-NMR and IR spectroscopy mentioned below that the pale yellow oily material is the compound D-12 mentioned above. The yield of the product was about 89%.

$^1$H-NMR (using CDCl$_3$): δ 1.51 (s, 6H), 1.58 (s, 6H), 1.95 (s, 3H), 1.93-1.98 (m, 2H), 2.30-2.36 (m, 2H), 5.21-5.28 (m, 1H), 5.52 (d, 1H), 5.57-5.60 (m, 1H), 6.10-6.17 (m, 2H), and 6.51-6.58 (m, 1H).

IR (using NaCl): 3102, 2973, 1714, 1650, 1605, 1453, 1404, 1385, 1374, 1361, 1326, 1296, 1284, 1273, 1231, 1170, 1114, 1077, 1047, 1014, 986, 951, 898, 848, 815, 804, 781, 719, 655 and 572 cm$^{-1}$.

Synthesis Example 8

Synthesis of the Above-Mentioned Polymerizable Compound D-13

Initially, 7.8 g (60 mmol) of 1-piperazineethanol (reagent from Tokyo Kasei Kogyo Co., Ltd.) was added to 200 ml of dehydrated dichloromethane contained in a flask. After air in the flask was replaced with an argon gas, 13.7 g (150 mmol) of triethylamine was fed to the flask. After the mixture was cooled to about −10° C., 11.3 g (130 mmol) of acrylic acid chloride was gradually dropped into the flask so that the temperature of the system in the flask fell in a range of from −10 to −5° C., followed by agitation of the mixture for 2 hours at room temperature. After the precipitate was removed from the product by filtering, the filtrate was condensed, and 200 ml of acetone was added to the condensed filtrate, followed by agitation at room temperature. A yellow oily material, which was obtained by condensing the acetone solution, was refined by column chromatography (using 250 g of silica gel 60 from Kanto Kagaku). Thus, 3.8 g of a colorless oily material was obtained. It was confirmed from $^1$H-NMR and IR spectroscopy mentioned below that the colorless oily material is the compound D-13 mentioned above. The yield of the product was about 27%.

$^1$H-NMR (using CDCl$_3$): δ 2.54 (t, 4H), 2.71 (t, 2H), 3.54-3.60 (bs, 2H), 3.66-3.72 (bs, 2H), 4.30 (t, 2H), 5.67-5.72 (m, 1H), 5.83-5.87 (m, 1H), 6.15-6.17 (m, 1H), 6.25-6.31 (m, 1H), 6.38-6.44 (m, 1H), and 6.52-6.58 (m, 1H).

IR (using NaCl): 2945, 2814, 1723, 1650, 1613, 1441, 1410, 1365, 1296, 1270, 1234, 1191, 1160, 1115, 1055, 981, 811, 791 and 566 cm$^{-1}$.

In addition, the following marketed monomer compounds (a) to (g) were used for Comparative Examples 1-7.

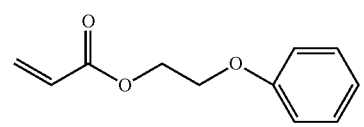

PHENOXYETHYL ACRYLATE

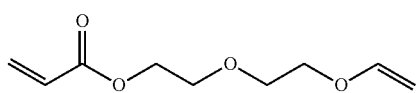

2-(2-VINYLOXYETHOXY)ETHYL ACRYLATE

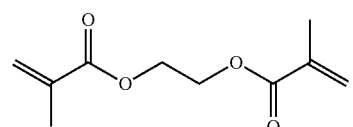

ETHYLENE GLYCOL DIMETHACRYLATE

-continued

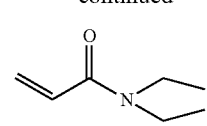

N,N-DIETHYLACRYLAMIDE
(d)

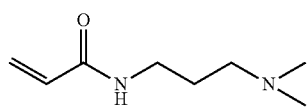

N-(3-DIMETHYLAMINOPROPYL)ACRYLAMIDE
(e)

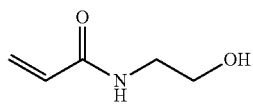

N-(2-HYDROXYETHYL)ACRYLAMIDE
(f)

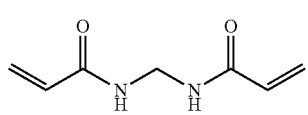

N,N'-METHYLENEBISACRYLAMIDE
(g)

Example 1

The following components were mixed using a magnetic stirrer to prepare a polymerizable material (clear ink) of Example 1.

| | |
|---|---|
| Polymerizable compound F-2 (synthesized in Synthesis Example 1) | 950 mg |
| Polymerization initiator (2-methyl-1-[4-(methylthio)phenyl]-2-morpholinopropane-1-one, IRGACURE 907 from BASF Japan Ltd.) | 50 mg |

Examples 2 to 8 and Comparative Examples 1 to 7

The procedure for preparation of the polymerizable material of Example 1 was repeated except that the polymerizable compound was replaced with a polymerizable compound described in Table 1 below to prepare polymerizable materials of Examples 2 to 8 and Comparative Examples 1 to 7.

Each of these polymerizable materials of Examples 1 to 8 and Comparative Examples 1 to 7 was evaluated with respect to the following properties.

1. Photo-Polymerizability

The photo-polymerizability of each polymerizable material was evaluated using an instrument (hereinafter referred to as Photo-DSC), which is a combination of a differential scanning calorimeter (DSC) DSC-7020 from Seiko Instruments Inc. and a spot light source LA-410UV from HAYASHI WATCH-WORKS. In this regard, UV light with a wavelength of 365 nm was used, and the light intensity was 200 mW/cm$^2$.

In this measurement, the amount of heat generated in the polymerization reaction caused by light irradiation was measured with the Photo-DSC. In this regard, the amount of heat generation was measured while irradiating the polymerizable material with the UV light for a sufficient time for completing the polymerization reaction of the polymerizable material, and then the light irradiation operation was performed again. In the first measurement, the amount of heat generation (first amount of heat generation) included both the amount of heat generated by the polymerization reaction and the amount of heat generated by the light irradiation. In the second measurement, the polymerized material was further irradiated with the UV light under the same condition to measure the amount of heat generated by the light irradiation (second amount of heat generation), thereby making it possible to determine the amount of heat generated by the polymerization reaction of the polymerizable material, which is difference between the first amount of heat generation and the second amount of heat generation.

In this heat generation property, the time (T1) between the start of the light irradiation and a time at which the amount of heat generation has a maximum value was measured to be used as an index of the speed of the photo-polymerization reaction.

2. Photo-Curability

The photo-curability of each polymerizable material was measured with an instrument (hereinafter referred to as Photo-Rheometer), which is a combination of a viscoelasticity measuring instrument VAR 200AD from REOLOGICA Instruments AB and a light emitting diode (LED) LIGHTNINGCURE LC-L1 from Hamamatsu Photonics K.K.

In this measurement, a sample (polymerizable material) was fed into a gap of 10 μm formed by a corn plate having a diameter of 20 mm. UV light with a wavelength of 365 nm and a light intensity of 50 mW/cm$^2$, which was emitted by the LED, irradiated the sample to determine change of the viscoelasticity of the sample caused by curing of the sample. In this regard, it was assumed that when the elastic modulus (in units of Pa) is saturated, the curing is completed. The maximum elastic modulus of the sample was determined from the measurement results to be used as an index of the photo-curability. In general, it can be said that when the elastic modulus of a sample is on the order of $1\times10^4$ Pa, the sample is fully cured. In addition, the amount of photo energy (curing energy), which was used until the elastic modulus was saturated, was determined as a product of the light intensity (i.e., 50 mW/cm$^2$) and the light irradiation time (in units of second).

3. Odor

An order sensory test was used for evaluating odor of a polymerizable material. The procedure is as follows.

(1) About 100 mg of a sample was contained in a 50 cc glass container, and then the container was capped;

(2) The container containing the sample was allowed to settle for 30 minutes at room temperature; and (3) By uncapping the container while smelling the sample at a point closer to the mouth of the container, the odor of the sample was evaluated. The odor was graded as follows.

⊚: The sample hardly smells. (Excellent)

○: The sample slightly smells but the smell is not unpleasant smell. (Good)

Δ: The sample smells unpleasantly. (Bad)

x: The sample seriously smells unpleasantly. (Worst)

TABLE 1

| | Polymerizable compound | Photo-polymerizability (T1, second) | Photo-curability Elastic modulus (Pa) | Photo-curability Curing energy (mJ/cm$^2$) | Odor |
|---|---|---|---|---|---|
| Ex. 1 | F-2 (prepared in Synthesis Ex. 1) | 4.8 | $1.0 \times 10^5$ | 799 | ○ |
| Ex. 2 | A-3 (prepared in Synthesis Ex. 2) | 4.8 | $1.0 \times 10^5$ | 177 | ⊚ |
| Ex. 3 | A-4 (prepared in Synthesis Ex. 3) | 3.6 | $1.0 \times 10^5$ | 134 | ⊚ |
| Ex. 4 | C-5 (prepared in Synthesis Ex. 4) | 3.0 | $1.0 \times 10^5$ | 144 | ○ |
| Ex. 5 | C-6 (prepared in Synthesis Ex. 5) | 6.0 | $1.0 \times 10^5$ | 180 | ○ |
| Ex. 6 | C-16 (prepared in Synthesis Ex. 6) | 4.8 | $1.0 \times 10^5$ | 146 | ○ |
| Ex. 7 | D-12 (prepared in Synthesis Ex. 7) | 6.0 | $1.0 \times 10^5$ | 158 | ⊚ |
| Ex. 8 | D-13 (prepared in Synthesis Ex. 8) | 3.6 | $1.0 \times 10^5$ | 142 | ⊚ |
| Comp. Ex. 1 | Phenoxyethyl acrylate (formula (a)) | 2.5 | $4.8 \times 10^4$ | 200 | X |
| Comp. Ex. 2 | 2-(vinyloxyethoxy) ethyl acrylate (formula (b)) | 1.8 | $1.0 \times 10^5$ | 146 | Δ |
| Comp. Ex. 3 | Ethylene glycol dimethacrylate (formula (c)) | 13.2 | $1.0 \times 10^5$ | 580 | Δ |
| Comp. Ex. 4 | N,N-diethyl-acrylamide (formula (d)) | 4.8 | $1.0 \times 10^5$ | 208 | X |
| Comp. Ex. 5 | N-(3-dimethylamino-propyl)acrylamide (formula (e)) | 3.6 | $1.0 \times 10^5$ | 244 | X |
| Comp. Ex. 6 | N-(2-hydroxyethyl)-acrylamide (formula (f)) | The initiator was not dissolved in the polymerizable compound, and therefore the evaluation could not be performed. | | | |
| Comp. Ex. 7 | N,N'-methylenebis-acrylamide (formula (g)) | The polymerizable compound was a solid at room temperature, and therefore the evaluation could not be performed. | | | |

It is clear from Table 1 that the polymerizable materials (clear inks) of Examples 1 to 8 have as good combination of photo-polymerizability and photo-curability while having no odor problem, and therefore the inks have good practicality. Among the inks, the inks of Examples 2 to 8 have small curing energy. It is considered that since both an acrylamide group and a (meth)acrylic acid ester group are present in a molecule of the polymerizable compounds, the inks have a good combination of photo-polymerizability and photo-curability while having no odor problem. In addition, the inks of Examples 2, 3, 7 and 8 are superior in odor, i.e., the inks hardly smell. Further, since the inks of Examples 2, 3 and 8 are superior in photo-polymerizability and photo-curability, the inks have excellent practicality.

The ink of Example 1 includes a polymerizable compound having an acrylamide group and an allyl group in a molecule thereof, and therefore the ink has a relatively low photo-curability. However, since the ink has good photo-polymerizability while having no odor problem, the ink can be used as a curable ink.

Next, color inks (black inks and blue inks) were prepared using the polymerizable compounds of Examples 1, 2, 3, 6 and 8, and then evaluated.

Specifically, the following components were mixed to prepare black inks.

| | |
|---|---|
| Polymerizable compound (polymerizable compounds of Examples 1, 2, 3, 6 or 8) | 100 parts |

-continued

| | |
|---|---|
| Polymerization initiator (2-methyl-1-[4-(methylthio)phenyl]-2-morpholinopropane-1-one, IRGACURE 907 from BASF Japan Ltd.) | 10 parts |
| Pigment (black pigment, MICROLITH BLACK C-K (carbon black) from BASF Japan Ltd.; or blue pigment, MICROLITH BLUE 4G-K from BASF Japan Ltd.) | 3 parts |

Thus, four black inkjet inks and four blue inkjet inks were prepared.

Each of the inkjet inks was ejected from inkjet nozzles toward a slide glass to form a layer of the ink on the slide glass. Next, UV light with an intensity of 200 mW/cm$^2$ irradiated each ink layer using an UV irradiator LH6 from Fusion Systems Japan Co., Ltd. to cure the ink layer. As a result, it was confirmed that each ink can be ejected from inkjet nozzles without any problems, and the ink layers can be fully cured.

Further, after a dip pen was dipped into each ink, and then character images were written on a plain paper and a PET (polyethylene terephthalate) film, the character images were irradiated with UV light with an intensity of 200 mW/cm$^2$ emitted by the UV irradiator LH6 from Fusion Systems Japan Co., Ltd. As a result, it was confirmed that the ink images are fully cured.

In contrast, the comparative inks of Comparative Examples 1 to 5 have unpleasant odor, and therefor have no practicality. For example, the acrylic acid esters and acrylamide of the polymerizable compounds used for the comparative inks of Comparative Examples 1, 4 and 5 have a good combination of photo-polymerizability and photo-curability, but have strong unpleasant odor. Therefore, the inks cannot be used as a curable ink. In addition, the comparative ink of Comparative Example 3, which includes a polymerizable compound having two methacrylic acid ester groups in a molecule, also has unpleasant odor (although the odor is slightly improved) while being inferior in photo-polymerizability and photo-curability. Further, the comparative ink of Comparative Example 2, which includes a polymerizable compound having an acrylic acid ester group and a vinyl group in a molecule, has excellent photo-polymerizability and photo-curability, but has unpleasant odor. In Comparative Example 6, the polymerizable compound cannot dissolve the polymerization initiator because the polymerizable compound has too high hydrophilicity due to the hydroxyl group therein. Therefore, it is hard to use the polymerizable compound in combination with a variety of organic compounds when preparing a curable ink. In Comparative Example 7, since the polymerizable compound has two acrylamide groups in a molecule thereof, the compound has too high an intermolecular interaction, and therefore the compound is a solid at room temperature. Therefore, it is hard to use the polymerizable compound for a curable ink.

It can be easily understood from comparison of the inks of Examples 1-8 with the comparative inks of Comparative Examples 1-7 that the inks including a polymerizable compound (monomer compound) of this disclosure have a good combination of photo-polymerizability and photo-curability without causing the odor problem. This is because the polymerizable compound has an acrylamide group and a group other than the acrylamide group (such as a (meth)acrylic acid ester group) in a molecule thereof, and therefore the reactivity and the intermolecular interaction of the polymerizable compound can be satisfactorily controlled, thereby making it possible to impart a good combination of photo-polymerizability, photo-curability and odor characteristic to the polymerizable compound.

As mentioned above, the ink of this disclosure, which includes a polymerizable compound of this disclosure, has a good combination of photo-polymerizability, photo-curability and odor characteristic. Further, the compound having formula (8) has a low skin irritation property. Specifically, the PII (primary skin irritation index) of the compound having formula (8), which is determined by the primary skin irritation test defined in OECD TG403, is 0.3 (i.e., no irritation). In addition, the compound has a low skin sensitization property. Specifically the SI (stimulation index) of the compound having formula (8), which is determined by the skin sensitization test defined in OECD TG442B, is 1.5 (no skin sensitization). Therefore, the ink including the polymerizable compound having formula (8) has good safeness as well as good practicality.

Effects of this Disclosure

According to this disclosure, a polymerizable compound and an ink are provided which have a good combination of photo-polymerizability and photo-curability while hardly smell.

Additional modifications and variations of the present invention are possible in light of the above teachings. It is therefore to be understood that within the scope of the appended claims the invention may be practiced other than as specifically described herein.

What is claimed is:
1. An ink comprising:
a colorant; and
a polymerizable compound,
wherein the polymerizable compound has the following formula (3) or (4):

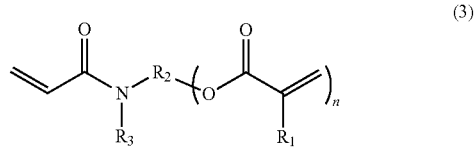

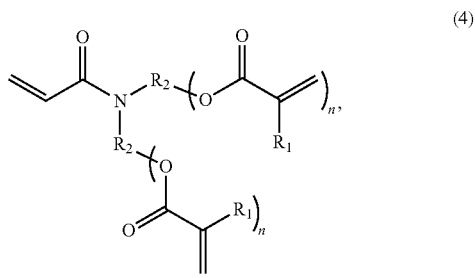

wherein $R_1$ represents a hydrogen atom or a methyl group; $R_2$ represents a divalent or trivalent group having 1 to 15 carbon atoms, which optionally includes a ring structure and a hetero atom; $R_3$ represents an alkyl group having 1 to 15 carbon atoms, which optionally includes a ring structure and a hetero atom; and n is 1 or 2.

2. The ink according to claim 1, wherein the viscosity of the ink is from 7 to 25 mPa·s.

3. An ink cartridge comprising:
a container; and
the ink according to claim 1, which is contained in the container.

4. A print comprising:
a support; and
an image formed on the support by the ink according to claim 1.

5. An ink comprising:
a colorant; and
a polymerizable compound,
wherein the polymerizable compound has the following formula (5) or (6):

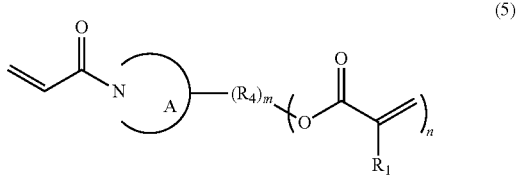

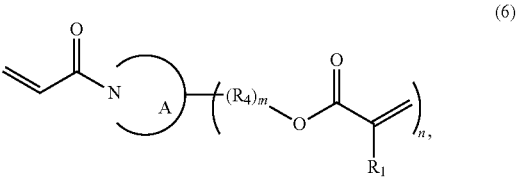

wherein $R_1$ represents a hydrogen atom or a methyl group; $R_4$ represents a divalent or trivalent group having 1 to 15 carbon atoms, which optionally includes a ring structure and a hetero atom; A represents a group having a ring structure having at least one nitrogen atom; n is 2; and m is 0 or 1.

6. The ink according to claim 5, wherein the group A includes a piperazine ring.

7. The ink according to claim 5,
wherein the viscosity of the ink is from 7 to 25 mPa·s.

8. An ink cartridge comprising:
a container; and
the ink according to claim 5, which is contained in the container.

9. An inkjet recording apparatus comprising:
the ink according to claim 8; and
an inkjet recording device to eject droplets of the ink contained in the ink cartridge to form an ink image on a recording medium.

10. The inkjet recording apparatus according to claim 9, further comprising:
an active energy ray irradiator to irradiate the ink image with an active energy ray.

11. A print comprising:
a support; and
an image formed on the support by the ink according to claim 5.

* * * * *